(12) United States Patent
Heinrich et al.

(10) Patent No.: US 8,993,564 B2
(45) Date of Patent: Mar. 31, 2015

(54) 7-AZAINDOLE DERIVATIVES SUITABLE FOR TREATMENT OF CANCERS

(75) Inventors: Timo Heinrich, Gross-Umstadt (DE); Margarita Wucherer-Plietker, Messel (DE); Hans-Peter Buchstaller, Griesheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/126,857

(22) PCT Filed: May 29, 2012

(86) PCT No.: PCT/EP2012/002262
§ 371 (c)(1),
(2), (4) Date: Dec. 17, 2013

(87) PCT Pub. No.: WO2012/175168
PCT Pub. Date: Dec. 27, 2012

(65) Prior Publication Data
US 2014/0187551 A1 Jul. 3, 2014

(30) Foreign Application Priority Data

Jun. 24, 2011 (DE) .......................... 10 2011 105 469

(51) Int. Cl.
*A61K 31/535* (2006.01)
*C07D 471/04* (2006.01)
*A61K 31/437* (2006.01)
*A61K 31/5377* (2006.01)
*A61K 45/06* (2006.01)

(52) U.S. Cl.
CPC ............. *C07D 471/04* (2013.01); *A61K 31/437* (2013.01); *A61K 31/5377* (2013.01); *A61K 45/06* (2013.01)
USPC ......... 514/234.5; 514/300; 544/127; 546/113

(58) Field of Classification Search
None
See application file for complete search history.

(56) References Cited

U.S. PATENT DOCUMENTS

| 8,420,820 B2 | 4/2013 | Wucherer-Plietker et al. |
| 2011/0218198 A1 | 9/2011 | Wucherer-Plietker et al. |

FOREIGN PATENT DOCUMENTS

| DE | 102008031517 A1 | 1/2010 |
| WO | WO 2010020308 A1 * | 2/2010 |

OTHER PUBLICATIONS

International Search Report from PCT/EP2012/002262 dated Sep. 11, 2012.

* cited by examiner

*Primary Examiner* — Wu-Cheng Winston Shen
*Assistant Examiner* — Jean Cornet
(74) *Attorney, Agent, or Firm* — Millen, White, Zelano & Branigan, P.C.

(57) ABSTRACT

Compounds of the formula (I) in which $R^1$, $R^2$ and $R^3$ have the meanings indicated in Claim 1, are inhibitors of PDK1 and cell proliferation/cell vitality and can be employed treatment of tumours.

10 Claims, No Drawings

7-AZAINDOLE DERIVATIVES SUITABLE FOR TREATMENT OF CANCERS

The invention relates to compounds of the formula I

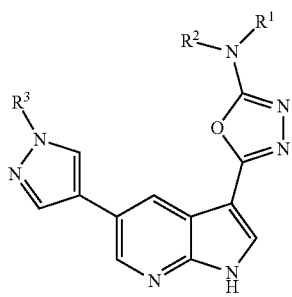

in which
R$^1$ denotes H, A, CH$_2$CN, CH$_2$CONH$_2$, CH$_2$CONHA', CH$_2$CONA'$_2$, CH$_2$COOH, CH$_2$COOA' or CH$_2$COHet$^1$,
R$^2$ denotes (CH$_2$)$_n$Ar, COAr, (CH$_2$)$_n$Het, Cyc, Alk or A,
R$^3$ denotes CH$_3$ or (CH$_2$)$_n$NHCOOA',
R$^4$ denotes phenyl,
Alk denotes unbranched or branched alkenyl having 2-6 C atoms,
A denotes unbranched or branched alkyl having 1-8 C atoms, in which one or two non-adjacent CH$_2$ and/or CH groups may be replaced by O, N and/or S atoms and/or 1-7H atoms may be replaced by F and/or Cl,
A' denotes unbranched or branched alkyl having 1-4 C atoms,
Cyc denotes cycloalkyl having 3-7 C atoms,
Ar denotes phenyl which is unsubstituted or mono-, di- or trisubstituted by Hal, A, (CH$_2$)$_2$CN, (CH$_2$)$_2$COOH, (CH$_2$)$_2$COOA, (CH$_2$)$_2$OH, (CH$_2$)$_2$OA, COHet$^1$, O(CH$_2$)$_2$R$^4$, NO$_2$, CONHHet$^1$, NHCOCyc, CONH(CH$_2$)$_2$CONH$_2$, CONH(CH$_2$)$_2$CONHA', CONH(CH$_2$)$_2$CONA'$_2$, CONH$_2$, CONHA', CONA'$_2$, NHCOAlk, CONHCH(R$^4$)CONH$_2$, CONH(CH$_2$)$_n$CONHHet$^1$, CONH(CH$_2$)$_n$COHet$^1$ and/or CONH(CH$_2$)$_n$Cyc,
Het denotes a mono- or bicyclic aromatic heterocycle having 1 to 4 N, and/or O and/or S atoms which is unsubstituted or mono- or disubstituted by Hal and/or A,
Het$^1$ denotes a monocyclic saturated, unsaturated or aromatic heterocycle having 1 to 4 N, and/or O and/or S atoms which is unsubstituted or mono- or disubstituted by A,
Hal denotes F, Cl, Br or I,
n denotes 0, 1 or 2,
and pharmaceutically usable salts, tautomers and stereoisomers thereof, including mixtures thereof in all ratios.

The invention was based on the object of finding novel compounds having valuable properties, in particular those which can be used for the preparation of medicaments.

It has been found that the compounds of the formula I and salts, tautomers and stereoisomers thereof, including mixtures thereof in all ratios, have very valuable pharmacological properties while being well tolerated.

In particular, they exhibit a cell proliferation/cell vitality-inhibiting action as antagonists or agonists. The compounds according to the invention can therefore be used for the combating and/or treatment of tumours, tumour growth and/or tumour metastases.

The antiproliferative action can be tested in a proliferation assay/vitality assay.

Accordingly, the compounds according to the invention or a pharmaceutically acceptable salt thereof are administered for the treatment of cancer, including solid carcinomas, such as, for example, carcinomas (for example of the lungs, pancreas, thyroid, bladder or colon), myeloid diseases (for example myeloid leukaemia) or adenomas (for example villous colon adenoma).

The tumours furthermore include monocytic leukaemia, brain, urogenital, lymphatic system, stomach, laryngeal and lung carcinoma, including lung adenocarcinoma and small-cell lung carcinoma, pancreatic and/or breast carcinoma.

The compounds are furthermore useful in the treatment of immune deficiency induced by HIV-1 (Human Immunodeficiency Virus Type 1).

Cancer-like hyperproliferative diseases are to be regarded as brain cancer, lung cancer, squamous epithelial cancer, bladder cancer, stomach cancer, pancreatic cancer, liver cancer, renal cancer, colorectal cancer, breast cancer, head cancer, neck cancer, oesophageal cancer, gynaecological cancer, thyroid cancer, lymphomas, chronic leukaemia and acute leukaemia. In particular, cancer-like cell growth is a disease which represents a target of the present invention. The present invention therefore relates to compounds according to the invention as medicaments and/or medicament active compounds in the treatment and/or prophylaxis of the said diseases and to the use of compounds according to the invention for the preparation of a pharmaceutical for the treatment and/or prophylaxis of the said diseases and to a process for the treatment of the said diseases comprising the administration of one or more compounds according to the invention to a patient in need of such an administration.

It can be shown that the compounds according to the invention have an antiproliferative action. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both the prevention of diseases and the treatment of pre-existing conditions. The prevention of proliferation/vitality is achieved by administration of the compounds according to the invention prior to the development of overt disease, for example for preventing tumour growth. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of a human disease.

The susceptibility of a particular cell to treatment with the compounds according to the invention can be determined by in vitro testing. Typically, a culture of the cell is incubated with a compound according to the invention at various concentrations for a period of time which is sufficient to allow the active agents to induce cell death or to inhibit cell proliferation, cell vitality or migration, usually between about one hour and one week. In vitro testing can be carried out using cultivated cells from a biopsy sample. The amount of cells remaining after the treatment are then determined.

The dose varies depending on the specific compound used, the specific disease, the patient status, etc. A therapeutic dose is typically sufficient considerably to reduce the undesired cell population in the target tissue, while the viability of the patient is maintained. The treatment is generally continued until a considerable reduction has occurred, for example an at least about 50% reduction in the cell burden, and may be continued until essentially no more undesired cells are detected in the body.

There are many diseases associated with deregulation of cell proliferation and cell death (apoptosis). The conditions of interest include, but are not limited to, the following. The compounds according to the invention are suitable for the treatment of various conditions where there is proliferation and/or migration of smooth muscle cells and/or inflammatory cells into the intimal layer of a vessel, resulting in restricted blood flow through that vessel, for example in the case of neointimal occlusive lesions. Occlusive graft vascular diseases of interest include atherosclerosis, coronary vascular disease after grafting, vein graft stenosis, perianastomatic prosthetic restenosis, restenosis after angioplasty or stent placement, and the like.

The compounds of the formula I, also act as regulators, modulators or inhibitors of protein kinases, in particular of the serine/threonine kinase type, which include, inter alia, phosphoinositide-dependent kinase 1 (PDK1). The compounds according to the invention exhibit a certain action in the inhibition of the serine/threonine kinases PDK1, IKK and TBK1.

PDK1 phosphorylates and activates a sub-group of the AGC protein kinase family, comprising PKB, SGK, S6K and PKC isoforms. These kinases are involved in the PI3K signal transduction pathway and control basic cellular functions, such as survival, growth and differentiation. PDK1 is thus an important regulator of diverse metabolic, proliferative and life-sustaining effects.

The compounds according to the invention also exhibit TGF receptor I kinase-inhibiting properties.

A number of diseases have been associated with TGF-β1 overproduction. Inhibitors of the intracellular TGF-β signalling pathway are suitable treatments for fibroproliferative diseases. Specifically, fibroproliferative diseases include kidney disorders associated with unregulated TGF-β activity and excessive fibrosis including glomerulonephritis (GN), such as mesangial proliferative GN, immune GN and crescentic GN. Other renal conditions include diabetic nephropathy, renal interstitial fibrosis, renal fibrosis in transplant patients receiving cyclosporin, and HIV-associated nephropathy. Collagen vascular disorders include progressive systemic sclerosis, polymyositis, sclerodermatitis, dermatomyositis, eosinophilic fasciitis, morphea, or those associated with the occurrence of Raynaud's syndrome. Lung fibroses resulting from excessive TGF-β activity include adult respiratory distress syndrome, idiopathic pulmonary fibrosis, and interstitial pulmonary fibrosis often associated with autoimmune disorders, such as systemic lupus erythematosus and sclerodermatitis, chemical contact or allergies. Another autoimmune disorder associated with fibroproliferative characteristics is rheumatoid arthritis.

Eye diseases associated with a fibroproliferative condition include proliferative vitreoretinopathy occurring during retinal reattachment surgery, cataract extraction with intraocular lens implantation, and post-glaucoma drainage surgery and are associated with TGF-β1 overproduction.

WO 2010/000364 A1 describes other azaindole derivatives for the treatment of tumours.

WO 2009/071577 describes other oxadiazole derivatives for the treatment of neurological, psychiatric and gastrointestinal diseases.

WO 2010/020308 describes other azaindole derivatives for the treatment of tumours. The compounds according to the invention have an unexpected advantage compared with the compounds from WO 2010/020308 (Table I).

Other azaindole derivatives are disclosed in US 2008/0021217 and in WO 2006/004984.

KKε and TBK1 are serine/threonine kinases which are highly homologous to one another and to other IkB kinases. The two kinases play an integral role in the innate immune system. Double-stranded RNA viruses are recognised by the Toll-like receptors 3 and 4 and the RNA helicases RIG-I and MDA-5 and result in activation of the TRIF-TBK1/IKKε-IRF3 signalling cascade, which results in a type I interferon response.

In 2007, Boehm et al. described IKKε as a novel breast cancer oncogene [J. S. Boehm et al., Cell 129, 1065-1079, 2007]. 354 kinases were investigated with respect to their ability to recapitulate the Ras-transforming phenotype together with an activated form of the MAPK kinase Mek. IKKε was identified here as a cooperative oncogene.

In addition, the authors were able to show that IKBKE is amplified and overexpressed in numerous breast cancer cell lines and tumour samples. The reduction in gene expression by means of RNA interference in breast cancer cells induces apoptosis and impairs the proliferation thereof. Eddy et al. obtained similar findings in 2005, which underlines the importance of IKKε in breast cancer diseases [S. F. Eddy et al., Cancer Res. 2005; 65 (24), 11375-11383].

A protumorigenic effect of TBK1 was reported for the first time in 2006. In a screening of a gene library comprising 251,000 cDNA, Korherr et al. identified precisely three genes, TRIF, TBK1 and IRF3, which are typically involved in the innate immune defence as proangiogenic factors [C. Korherr et al., PNAS, 103, 4240-4245, 2006]. In 2006, Chien et al. [Y. Chien et al., Cell 127, 157-170, 2006] published that TBK1-/- cells can only be transformed to a limited extent using oncogenic Ras, which suggests an involvement of TBK1 in the Ras-mediated transformation. Furthermore, they were able to show that an RNAi-mediated knockdown of TBK1 triggers apoptosis in MCF-7 and Panc-1 cells. Barbie et al. recently published that TBK1 is of essential importance in numerous cancer cell lines with mutated K-Ras, which suggests that TBK1 intervention could be of therapeutic importance in corresponding tumours [D. A. Barbie et al., Nature Letters 1-5, 2009].

Diseases caused by protein kinases are characterised by anomalous activity or hyperactivity of such protein kinases. Anomalous activity relates to either: (1) expression in cells which do not usually express these protein kinases; (2) increased kinase expression, which results in undesired cell proliferation, such as cancer; (3) increased kinase activity, which results in undesired cell proliferation, such as cancer, and/or in hyperactivity of the corresponding protein kinases. Hyperactivity relates either to amplification of the gene which encodes for a certain protein kinase, or the generation of an activity level which can be correlated with a cell proliferation disease (i.e. the severity of one or more symptoms of the cell proliferation disease increases with increasing kinase level). The bioavailability of a protein kinase may also be influenced by the presence or absence of a set of binding proteins of this kinase.

The most important types of cancer that can be treated using a compound according to the invention include colorectal cancer, small-cell lung cancer, non-small-cell lung cancer, multiple myeloma as well as renal cell carcinoma and endometrium carcinoma, particularly also types of cancer in which PTEN is mutated, inter alia breast cancer, prostate cancer and glioblastoma.

In addition, the compounds according to the invention can be used to achieve additive or synergistic effects in certain existing cancer chemotherapies and radiotherapies and/or to restore the efficacy of certain existing cancer chemotherapies and radiotherapies.

Compounds of the formula I are also taken to mean the hydrates and solvates of these compounds, furthermore pharmaceutically usable derivatives.

The invention also relates to the optically active forms (stereoisomers), salts, the enantiomers, the racemates, the diastereomers and the hydrates and solvates of these compounds. Solvate of the compounds are taken to mean adductions of inert solvent molecules onto the compounds which form owing to their mutual attractive force. Solvate are, for example, mono- or dihydrates or alcoholates. The invention naturally also relates to the solvates of the salts of the compounds according to the invention.

Pharmaceutically usable derivatives are taken to mean, for example, the salts of the compounds according to the invention and also so-called prodrug compounds. Prodrug derivatives are taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active compound which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:
improved treatment, healing, prevention or elimination of a disease, syndrome, condition, complaint, disorder or side effects or also the reduction in the advance of a disease, condition or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I and pharmaceutically usable salts, tautomers and stereoisomers thereof, characterised in that a) for the preparation of compounds of the formula I in which $R^1$H and
$R^2$ has the meanings indicated in Claim 1,
a compound of the formula II

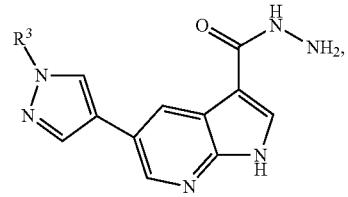

in which $R^3$ has the meaning indicated in Claim 1,
is reacted with a compound of the formula III

in which $R^2$ has the meaning indicated in Claim 1,
or
b) for the preparation of compounds of the formula I in which
$R^1$ denotes A, $CH_2CN$, $CH_2CONH_2$, $CH_2CONHA'$, $CH_2CONA'_2$, $CH_2COOH$, $CH_2COOA'$ or $CH_2COHet^1$ and
$R^2$ has the meanings indicated in Claim 1,
a compound of the formula IV,

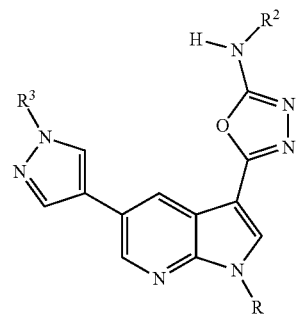

in which $R^2$ and $R^3$ have the meanings indicated in Claim 1 and R denotes an amino-protecting group,
is reacted with a compound of the formula V

in which L denotes Cl, Br, I, tosylate or mesylate,
and the amino-protecting group is cleaved off at the same time or subsequently,
and/or a base or acid of the formula I is converted into one of its salts.

Above and below, the radicals $R^1$, $R^2$ and $R^3$ have the meanings indicated for the formula I, unless expressly indicated otherwise.

A denotes alkyl, is unbranched (linear) or branched, and has 1, 2, 3, 4, 5, 6, 7 or 8 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

One or two CH and/or $CH_2$ groups in A may also be replaced by N, O or S atoms. A thus also denotes, for example, 2-methoxyethyl or 2-hydroxyethyl.

A furthermore preferably denotes unbranched or branched alkyl having 1-8 C atoms, in which one or two non-adjacent $CH_2$ and/or CH groups may be replaced by O, N and/or S atoms and/or 1-7H atoms may be replaced by F and/or Cl.

A' preferably denotes methyl, ethyl, propyl, isopropyl, butyl, isobutyl, sec-butyl or tert-butyl.

Cyc preferably denotes cyclopropyl, cyclobutyl, cyclopentyl or cyclohexyl, furthermore cycloheptyl.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-trifluoromethylphenyl, o-, m- or p-fluorophenyl, o-, m- or p-bromophenyl, o-, m- or p-chlorophenyl, o-, m- or p-hydroxyphenyl, o-, m- or p-methoxyphenyl, o-, m- or p-methylsulfonylphenyl, o-, m- or p-nitrophenyl, o-, m- or p-aminophenyl, o-, m- or p-methylaminophenyl, o-, m- or p-dimethylaminophenyl, o-, m- or p-aminosulfonylphenyl, o-, m- or p-methyl-aminosulfonylphenyl, o-, m- or p-aminocarbonylphenyl, o-, m- or p-carboxy-phenyl, o-, m- or p-methoxycarbonylphenyl, o-, m- or p-ethoxycarbonylphenyl o-, m- or p-acetylphenyl, o-, m- or p-formylphenyl, o-, m- or p-cyanophenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, p-iodophenyl, 4-fluoro-3-chlorophenyl, 2-fluoro-4-bromophenyl, 2,5-difluoro-4-bromophenyl or 2,5-dimethyl-4-chlorophenyl.

Alk denotes linear or branched alkenyl having 2, 3, 4, 5 or 6 C atoms.

Ar preferably denotes phenyl which is unsubstituted or mono-, di- or trisubstituted by Hal, A, $(CH_2)_2CN$, $(CH_2)_2COOH$, $(CH_2)_2COOA$, $(CH_2)_2OH$, $(CH_2)_2OA$, $COHet^1$, $O(CH_2)_2R^4$, $NO_2$, $CONHHet^1$, NHCOCyc, $CONH(CH_2)_2CONH_2$, $CONH(CH_2)_2CONHA'$, $CONH(CH_2)_2CONA'_2$, $CONH_2$, CONHA', $CONA'_2$, NHCOAlk, $CONHCH(R^4)CONH_2$, $CONH(CH_2)_nCONHHet^1$, $CONH(CH_2)_nCOHet^1$ and/or $CONH(CH_2)_nCyc$.

Irrespective of further substitutions, $Het^1$ denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated.

Unsubstituted $Het^1$ can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

$Het^1$ furthermore preferably denotes piperidinyl, pyrrolidinyl, morpholinyl, piperazinyl, imidazolidinyl, oxazolidinyl, tetrahydropyranyl, dihydroisoindolyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl or pyrazinyl, each of which is unsubstituted or mono- or disubstituted by A.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl.

Het furthermore preferably denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzodioxolyl, benzotriazolyl, quinolinyl, quinoxalinyl, quinazolinyl, pyrrolopyridinyl, purinyl, indolyl or indazolyl, each of which is unsubstituted or mono- or disubstituted by Hal and/or A.

Hal preferably denotes F, Cl or Br, but also I, particularly preferably F or Cl.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Ig, which conform to the formula I and in which the radicals not designated in greater detail have the meaning indicated for the formula I, but in which in Ia Het denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzodioxolyl, benzotriazolyl, quinolinyl, quinoxalinyl, quinazolinyl, pyrrolopyridinyl, purinyl, indolyl or indazolyl, each of which is unsubstituted or mono- or disubstituted by Hal and/or A;

in Ib $Het^1$ denotes piperidinyl, pyrrolidinyl, morpholinyl, piperazinyl, imidazolidinyl, oxazolidinyl, tetrahydropyranyl, dihydroisoindolyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl or pyrazinyl, each of which is unsubstituted or mono- or disubstituted by A;

in Ic $R^1$ denotes H, A, $CH_2CN$, $CH_2CONH_2$, $CH_2CONHA'$, $CH_2CONA'_2$, $CH_2COOH$, $CH_2COOA'$ or $CH_2COHet^1$, $R^2$ denotes $(CH_2)_nAr$, $COAr$, $(CH_2)_nHet$, Cyc, Alk or A, $R^3$ denotes $CH_3$ or $(CH_2)_nNHCOOA'$, $R^4$ denotes phenyl, Alk denotes unbranched or branched alkenyl having 2-6 C atoms, A denotes unbranched or branched alkyl having 1-8 C atoms, in which one or two non-adjacent $CH_2$ and/or CH groups may be replaced by O, N and/or S atoms and/or 1-7H atoms may be replaced by F and/or Cl, A' denotes unbranched or branched alkyl having 1-4 C atoms, Cyc denotes cycloalkyl having 3-7 C atoms, Ar denotes phenyl which is unsubstituted or mono-, di- or trisubstituted by Hal, A, $(CH_2)_2CN$, $(CH_2)_2COOH$, $(CH_2)_2COOA$, $(CH_2)_2OH$, $(CH_2)_2OA$, $COHet^1$, $O(CH_2)_2R^4$, $NO_2$, $CONHHet^1$, NHCOCyc, CONH$(CH_2)_2CONH_2$, $CONH(CH_2)_2CONHA'$, CONH$(CH_2)_2CONA'_2$, $CONH_2$, $CONHA'$, $CONA'_2$, NHCOAlk, $CONHCH(R^4)CONH_2$, CONH$(CH_2)_nCONHHet^1$, $CONH(CH_2)_nCOHet^1$ and/or $CONH(CH_2)_nCyc$, Het denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzodioxolyl, benzotriazolyl, quinolinyl, quinoxalinyl, quinazolinyl, pyrrolopyridinyl, purinyl, indolyl or indazolyl, each of which is unsubstituted or mono- or disubstituted by Hal and/or A, $Het^1$ denotes piperidinyl, pyrrolidinyl, morpholinyl, piperazinyl, imidazolidinyl, oxazolidinyl, tetrahydropyranyl, dihydroisoindolyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl or pyrazinyl, each of which is unsubstituted or mono- or disubstituted by A, Hal denotes F, Cl, Br or I, n denotes 0, 1 or 2;

and pharmaceutically usable salts, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], GeorgThieme-Verlag, Stuttgart), to be precise under reaction conditions which are known and suitable for the said reactions. Use can also be made here of variants known per se which are not mentioned here in greater detail.

Compounds of the formula I in which $R^1$H and $R^2$ has the meanings indicated in Claim 1, can preferably be obtained by reacting a compound of the formula II with a compound of the formula III.

The starting compounds of the formulae II and III are generally known. If they are novel, however, they can be prepared by methods known per se.

Depending on the conditions used, the reaction time is between a few minutes and 14 days, the reaction temperature is between about −30° and 140°, normally between 0° and 110°, in particular between about 60° and about 100°. Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to tert-butanol.

Compounds of the formula I in which $R^1$ denotes A, $CH_2CN$, $CH_2CONH_2$, $CH_2CONHA'$, $CH_2CONA'_2$, $CH_2COOH$, $CH_2COOA'$ or $CH_2COHet^1$ and $R^2$ has the meanings indicated in Claim 1, can preferably be obtained by reacting a compound of the formula IV with a compound of the formula V.

The starting compounds of the formulae IV and V are generally known. If they are novel, however, they can be prepared by methods known per se.

Depending on the conditions used, the reaction time is between a few minutes and 14 days, the reaction temperature is between about −30° and 140°, normally between 0° and 110°, in particular between about 60° and about 100°.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Particular preference is given to DMF.

The reaction is generally carried out in the presence of an acid-binding agent, preferably an organic base, such as DIPEA, triethylamine, dimethylaniline, pyridine or quinoline.

The addition of an alkali-metal or alkaline-earth metal hydroxide, carbonate or bicarbonate or or another salt of a weak acid of the alkali or alkaline-earth metals, preferably of potassium, sodium, calcium or caesium, may also be advantageous.

The amino-protecting group R is removed simultaneously or subsequently.

The expression "amino-protecting group" is known in general terms and relates to groups which are suitable for protecting (blocking) an amino group against chemical reactions, but are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The expression "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC and 2-iodoethoxycarbonyl; aralkoxycarbonyl, such as CBZ ("carbobenzoxy"), 4-methoxybenzyloxycarbonyl and FMOC; and arylsulfonyl, such as Mtr, Pbf and Pmc. Preferred amino—protecting groups are phenylsulfonyl, p-tolylsulfonyl, SEM [beta(trimethylsilyl)ethyl], further silyl groups, such as TIPS (triisoproylsilyl) or TBDMS (tert.-butyldimethylsilyl), benzyl, p-methoxybenzyl or o-nitro-benzyl.

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut, Pbf, Pmc and Mtr groups can, for example, preferably be cleaved off using TFA in dichloromethane or using approximately 3 to 5N HCl in dioxane at 15-30°, and the FMOC group can be cleaved off using an approximately 5 to 50% solution of dimethylamine, diethylamine or piperidine in DMF at 15-30°.

The trityl group is employed to protect the amino acids histidine, asparagine, glutamine and cysteine. They are cleaved off, depending on the desired end product, using TFA/10% thiophenol, with the trityl group being cleaved off from all the said amino acids; on use of TFA/anisole or TFA/thioanisole, only the trityl group of His, Asn and Gln is cleaved off, whereas it remains on the Cys side chain.

The Pbf (pentamethylbenzofuranyl) group is employed to protect Arg. It is cleaved off using, for example, TFA in dichloromethane.

Hydrogenolytically removable protecting groups (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline-earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active compound which comprises a compound of the formula I in the form of one of its salts, in particular if this salt form imparts improved pharmacokinetic properties on the active compound compared with the free form of the active compound or any other salt form of the active compound used earlier. The pharmaceutically acceptable salt form of the active compound can also provide this active compound for the first time with a desired pharmacokinetic property which it did not have earlier and can even have a positive influence on the pharmacodynamics of this active compound with respect to its therapeutic efficacy in the body.

The invention furthermore relates to medicaments comprising at least one compound of the formula I and/or pharmaceutically usable salts, tautomers and stereoisomers thereof, including mixtures thereof in all ratios, and optionally excipients and/or adjuvants.

Pharmaceutical formulations can be administered in the form of dosage units which comprise a predetermined amount of active compound per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active compound per dosage unit. Preferred dosage unit formulations are those which comprise a daily dose or part-dose, as indicated above, or a corresponding fraction thereof of an active compound. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active compound with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agaragar, calcium carbonate or sodium carbonate, can likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, tautomers and stereoisomers thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, tautomers and stereoisomers thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsiloncaprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active compound can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active compound can be employed either with a paraffinic or a water-miscible cream base. Alternatively, the active compound can be formulated to give a cream with an oil-in-water cream base or a water-in-oil base.

Pharmaceutical formulations adapted for topical application to the eye include eye drops, in which the active compound is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or pharmaceutically usable salts, tautomers and stereoisomers thereof, including mixtures thereof in all ratios, and at least one further medicament active compound.

The invention also relates to a set (kit) consisting of separate packs of (a) an effective amount of a compound of the formula I and/or pharmaceutically usable salts, tautomers and stereoisomers thereof, including mixtures thereof in all ratios, and (b) an effective amount of a further medicament active compound.

The set comprises suitable containers, such as boxes, individual bottles, bags or ampoules. The set may, for example, comprise separate ampoules, each containing an effective amount of a compound of the formula I and/or pharmaceutically usable salts, tautomers and stereoisomers thereof, including mixtures thereof in all ratios,
and an effective amount of a further medicament active compound in dissolved or lyophilised form.
Use The present compounds are suitable as pharmaceutical active compounds for mammals, especially for humans, in the treatment and control of cancer diseases.

The invention furthermore relates to the compounds of the formula I and pharmaceutically usable salts, tautomers and stereoisomers thereof, including mixtures thereof in all ratios, for use for the treatment of tumours, tumour growth, tumour metastases and/or AIDS.

The invention furthermore relates to the compounds of the formula I and pharmaceutically usable salts, tautomers and stereoisomers thereof, including mixtures thereof in all ratios, for use for the treatment of fibrosis, restenosis, HIV infection Alzheimer's, atherosclerosis and/or for the promotion of wound healing.

The present invention encompasses the use of the compounds of the formula I and/or physiologically acceptable salts, tautomers and stereoisomers thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma bowel cancer. A further group of preferred forms of cancer are monocytic leukaemia, lung adenocarcinoma, small-cell lung carcinomas, pancreatic cancer, glioblastomas and breast carcinoma.

Also encompassed is the use of the compounds of the formula I and/or physiologically acceptable salts, tautomers and stereoisomers thereof for the preparation of a medicament for the treatment and/or control of a tumour-induced disease in a mammal, in which to this method a therapeutically effective amount of a compound according to the invention is administered to a sick mammal in need of such treatment. The therapeutic amount varies according to the particular disease and can be determined by the person skilled in the art without undue effort.

Particular preference is given to the use for the treatment of a disease, where the disease is a solid tumour.

The solid tumour is preferably selected from the group of tumours of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx and/or the lung.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

The invention furthermore relates to the use of the compounds according to the invention for the treatment of bone pathologies, where the bone pathology originates from the group osteosarcoma, osteoarthritis and rickets.

The compounds of the formula I may also be administered at the same time as other well-known therapeutic agents that are selected for their particular usefulness against the condition that is being treated.

The present compounds are also suitable for combination with known anti-cancer agents. These known anti-cancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and further angiogenesis inhibitors. The present compounds are particularly suitable for administration at the same time as radiotherapy.

"Oestrogen receptor modulators" refers to compounds which interfere with or inhibit the binding of oestrogen to the receptor, regardless of mechanism.

Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)-ethoxy]phenyl]-2H-1-benzopyran-3-yl]phenyl 2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism.

Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism.

Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenylretinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)bis-mu-(hexane-1,6-diamine)-mu-[diamineplatinum(II)]bis-[diamine(chloro)platinum(II)]tetrachloride, diarisidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797.

Topoisomerase inhibitors are, for example, topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H, 15H)-dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]phenanthridinium, 6,9-bis[(2-amino-ethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides such as G3139, ODN698, RVASK-RAS, GEM231 and INX3001 and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichloro-phenyl)urea, N6-[4-deoxy-4-[N2-[2(E),4(E)-tetradecadienoyl]glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,1-diazatetracyclo(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

Evidence of the Action of Pharmacological Inhibitors on the Proliferation/Vitality of Tumour Cells In Vitro 1.0 Background In the present experiment description, the inhibition of tumour cell proliferation/tumour cell vitality by active compounds is described.

The cells are sown in a suitable cell density in microtitre plates (96-well format) and the test substances are added in the form of a concentration series. After four further days of cultivation in serum-containing medium, the tumour cell proliferation/tumour cell vitality can be determined by means of an Alamar Blue test system.

2.0 Experimental Procedure 2.1 Cell Culture

For example commercially available colon carcinoma cell lines, ovary cell lines, prostate cell lines or breast cell lines, etc.

The cells are cultivated in medium. At intervals of several days, the cells are detached from the culture dishes with the aid of trypsin solution and sown in suitable dilution in fresh medium. The cells are cultivated at 37° Celsius and 10% $CO_2$.

2.2. Sowing of the Cells

A defined number of cells (for example 2000 cells) per culture/well in a volume of 180 µl of culture medium are sown in microtitre plates (96 well cell-culture plates) using a multichannel pipette. The cells are subsequently cultivated in a CO2 incubator (37° C. and 10% CO2).

2.3. Addition of the Test Substances

The test substances are dissolved, for example, in DMSO and subsequently employed in corresponding concentration (if desired in a dilution series) in the cell culture medium. The dilution steps can be adapted depending on the efficiency of the active compounds and the desired spread of the concentrations. Cell culture medium is added to the test substances in corresponding concentrations. The addition of the test substances to the cells can take place on the same day as the sowing of the cells. To this end, in each case 20 µl of substance solution from the predilution plate are added to the cultures/wells. The cells are cultivated for a further 4 days at 37° Celsius and 10% $CO_2$.

2.4. Measurement of the Colour Reaction

In each case, 20 µl of Alamar Blue reagent are added per well, and the microtitre plates are incubated, for example, for a further seven hours in a CO2 incubator (at 37° C. and 10% CO2). The plates are measured in a reader with a fluorescence filter at a wavelength of 540 nm. The plates can be shaken gently immediately before the measurement.

3. Evaluation

The absorbance value of the medium control (no cells and test substances used) is subtracted from all other absorbance values. The controls (cells without test substance) are set equal to 100 percent, and all other absorbance values are set in relation thereto (for example in % of control):

Calculation:

100*(value with cells and test substance−value of medium control) (value with cells−value of medium control)

$IC_{50}$ values (50% inhibition) are determined with the aid of statistics programs, such as, for example, RS1.

4.0 Test for the Inhibition of PDK1

The experimental batches are carried out in a flashplate system with 384 wells/microtitration plate.

In each case, the PDK1 sample $His_6$-PDK1(1-50)(3.4 nM), the PDK1 substrate biotin-bA-bA-KTFCGTPEYLAPEVR-REPRILSEEEQEMFRDFDYIADWC (400 nM), 4 µM ATP (with 0.2 µCi of $^{33}$P-ATP/well) and the test substance in 50 µl of conventional experimental solution per well are incubated at 30° C. for 60 min. The test substances are employed in corresponding concentrations (if desired in a dilution series).

The control is carried out without test substance. The reaction is stopped using standard methods and washed. The activity of the kinase is measured via the incorporated radioactivity in top count. In order to determine the non-specific kinase reaction (blank value), the experimental batches are carried out in the presence of 100 nM staurosporine.

5.0 Evaluation

The radioactivity (decompositions per minute) of the blank value (no use of test substance in the presence of staurosporine) is subtracted from all other radioactivity values. The controls (kinase activity without test substance) are set equal to 100 percent and all other radioactivity values (after subtracting the blank value) are expressed set in relation thereto (for example in % of the control).

Calculation:

$$\frac{100 * (\text{value of the kinase activity with test substance} - \text{blank value})}{(\text{value of the control} - \text{blank value})} = \% \text{ of the control}$$

$IC_{50}$ values (50% inhibition) are determined with the aid of statistics programmes, such as, for example, RS1. $IC_{50}$ data of compounds according to the invention are indicated in Table 1.

| Material | Order No. | Manufacturer |
| --- | --- | --- |
| Microtitre plates for cell culture (Nunclon Surface 96-well plate) | | 167008 Nunc |
| DMEM | P04-03550 | Pan Biotech |
| PBS (10x) Dulbecco | 14200-067 | Gibco |
| 96-well plates (polypropylene) | | 267334 Nunc |
| AlamarBlue ™ | BUF012B | Serotec |
| FCS | 1302 | Pan Biotech GmbH |
| Trypsin/EDTA solution 10x | L 2153 | Biochrom AG |
| 75 $cm^2$ culture bottles | 353136 | BD Falcon |
| A2780 | 93112519 | ECACC |
| Colo205 | CCL222 | ATCC |
| MCF7 | HTB22 | ATCC |
| PC3 | CRL-1435 | ATCC |
| 384-well flash plates | SMP410A001PK | Perkin Elmer |

APCI-MS (atmospheric pressure chemical ionisation-mass spectrometry) $(M + H)^+$.
$IC_{50}$ data of compounds according to the invention are indicated in Table 1.

IKK—Kinase Test (IKKepsilon)

The kinase assay is performed as 384-well flashplate assay.

1 nM IKK, 800 nM biotinylated I B (19-42) peptide (biotin-C6-C6-GLKKERLLDDRHDSGLDSMKDEE) and 10 µM ATP (with 0.3 µCi of $^{33}$P-ATP/well) are incubated in a total volume of 50 µl (10 mM MOPS, 10 mM magnesium acetate, 0.1 mM EGTA, 1 mM dithiothreitol, 0.02% of Brij35, 0.1% of BSA, 0.1% of BioStab, pH 7.5) with or without test substance at 30° C. for 120 min.

The reaction is stopped using 25 µl of 200 mM EDTA solution, filtered off with suction after 30 min at room temperature, and the wells are washed 3 times with 100 µl of 0.9% NaCl solution. The non-specific proportion of the kinase reaction (blank) is determined using 3 µM EMD 1126352 (BX-795). Radioactivity is measured in the Topcount. $IC_{50}$ values are calculated using RS1.

TBK1—Kinase Test

The kinase assay is performed as 384-well flashplate assay.

0.6 nM TANK binding kinase (TBK1), 800 nM biotinylated MELK-derived peptide (biotin-Ah-Ah-AKP-KGNKDYHLQTCCGSLAYRRR) and 10 µM ATP (with 0.25 µCi of $^{33}$P-ATP/well) are incubated in a total volume of 50 µl (10 mM MOPS, 10 mM magnesium acetate, 0.1 mM EGTA, 1 mM DTT, 0.02% of Brij35, 0.1% of BSA, pH 7.5)

with or without test substance at 30° C. for 120 min. The reaction is stopped using 25 μl of 200 mM EDTA solution, filtered off with suction after 30 min at room temperature, and the wells are washed 3 times with 100 μl of 0.9% NaCl solution. The non-specific proportion of the kinase reaction (blank) is determined using 100 nM staurosporine. Radioactivity is measured in the Topcount. $IC_{50}$ values are calculated using RS1.

In-vitro (Enzyme) Assay for Determination of the Efficacy of the Inhibitors of the Inhibition of TGF-Beta-Mediated Effects As an example, the ability of the inhibitors to eliminate TGF-beta-mediated growth inhibition is tested.

Cells of the lung epithelial cell line MvlLu are sown in a defined cell density in a 96-well microtitre plate and cultivated overnight under standard conditions. Next day, the medium is replaced by medium which comprises 0.5% of FCS and 1 ng/ml of TGF-beta, and the test substances are added in defined concentrations, generally in the form of dilution series with 5-fold steps. The concentration of the solvent DMSO is constant at 0.5%. After a further two days, Crystal Violet staining of the cells is carried out. After extraction of the Crystal Violet from the fixed cells, the absorption is measured spectrophotometrically at 550 nm. It can be used as a quantitative measure of the adherent cells present and thus of the cell proliferation during the culture.

HPLC/MS Method:
Equipment: Agilent 1200 series
Column: Chromolith SpeedROD RP-18e, 50×4.6 mm$^2$
Flow rate: 2.4 ml/min
Eluent A: water+0.05% of formic acid
Eluent B: acetonitrile+0.04% of formic acid
Wavelength: 220 nm
Method: polar
Gradient:
0 min: 4% of B, 2.8 min: 100% of B; 3.3 min 100% of B; 3.4 min 4% of B
Mass spectroscopy: positive mode
m.p.=melting point
MS (ESI): mass spectroscopy (electrospray ionisation)

Scheme 1 below shows an overview of how compounds from the present application can be prepared.

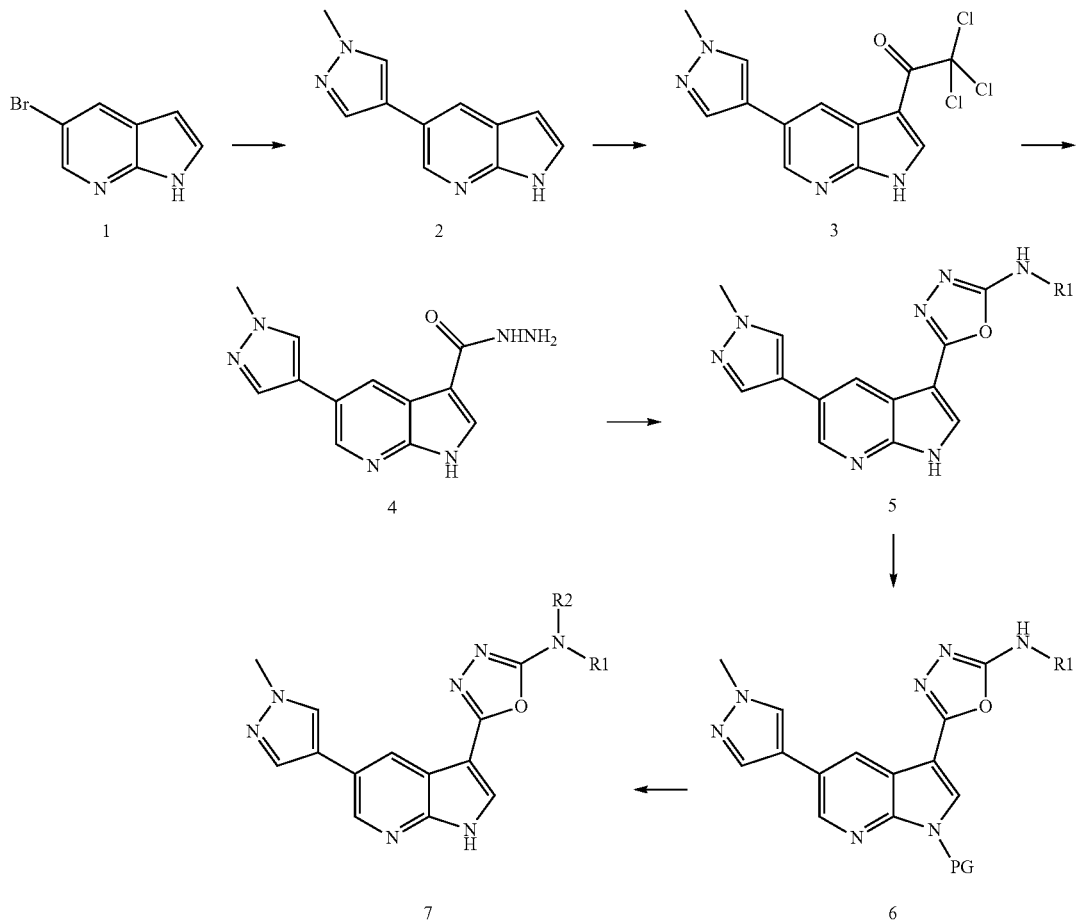

Scheme 1

Commercially available 5-bromo-7-azaindole 1 is coupled to methylpyrazoleboronic acid ester under Suzuki conditions to give 2. This reagent is prepared from bromomethylpyrazole and pinacolatodiborane. The indole derivative 2 is acylated in position 3 under Friedl-Crafts conditions to give intermediate 3. The reaction with hydrazine gives hydrazide 4, which is reacted with isothiocyanates to give oxadiazoles 5. Isothiocyanates are in some cases commercially available or can be prepared by processes known from the literature. The indole NH in 5 can be protected selectively under suitable conditions, giving 6 [see E) below]. The protecting group can then immediately be cleaved off under optimised reaction conditions with derivatisation of the bridge nitrogen. Alternatively, $R^1$ in 5 can be reacted further without using a protecting group (see F) below).

A)

Synthesis of 5-(1-methyl-1H-pyrazol-4-yl)-1H-pyrolo[2,3-b]pyridine 2

25 g of 5-bromo-1H-pyrrolo[2,3-b]pyridine 1 and 40 g of 1-methyl-4-(4,4,5,5-tetramethyl-1,3,2-dioxaborolan-2-yl)-1H-pyrazole are dissolved 350 ml of DMF, and 20 g of tetrakis(triphenylphosphine)palladium are added under protective gas. After addition of 190 ml of 2N sodium carbonate solution, the batch is stirred at 100° C. for 12 h. All volatile constituents are removed in vacuo, and the residue is partitioned between ethyl acetate and water. Insoluble constituents are filtered off. After extraction of the aqueous phase, the combined organic phases are dried over sodium sulfate, filtered and evaporated to ¼ of the volume in vacuo. The crystal batch formed after 12 h at 0° C. is filtered off and combined with the first solid fraction, giving 22.7 g of compound 2; HPLC-MS: Rt=1.400 min; [M+H+]: 199.1.

B)

Synthesis of 2,2,2-trichloro-1-[5-(1-methyl-1H-pyrazol-4-yl)-1H-pyrrolo[2,3-b]-pyridin-3-yl]ethanone 3

76.3 g of $AlCl_3$ are suspended in 600 ml of dichloroethane under argon, and 22.7 g of the product 2 prepared above are incorporated in portions. During this addition, the orange solution changes colour to dark brown. After 10 min, 19.2 ml of trichloroacetyl chloride are slowly added dropwise. The reaction batch is cooled here using a water bath. When the addition is complete, the mixture is stirred at RT for a further 6 h before the suspension is filtered off with suction and the filter cake is washed with dichloromethane and water. The filter cake is transferred into a flask, and water is carefully added with ice-water cooling. The beige solid is filtered off with suction, likewise rinsed and subsequently dried at 70° C. in a vacuum drying cabinet for 3 h, giving 20.6 g. The acidic mother liquor is poured into ice-water, the suspension is likewise filtered off with suction as described above and dried, giving 10.3 g. The mother liquor is left to stand for 12 h, and precipitated product is filtered off with suction and dried, giving 0.4 g. The solids are combined; HPLC-MS: Rt=2.132 min; [M+H+]: 345.0.

C)

Synthesis of 5-(1-methyl-1H-pyrazol-4-yl)-1H-pyrolo[2,3-b]pyridine-3-carbohydrazide 4

8 g of the trichloroethanone 3 prepared above are suspended in 150 ml of methanol, and 34 ml of hydrazine hydrate are slowly added dropwise at 5-10° C. When the addition is complete, the mixture is stirred at RT for a further 1 h. Half of the liquid components are subsequently removed in vacuo, and the residue is cooled to 0° C. The precipitating crystals are filtered off with suction and washed with methanol. The residue is subsequently dried at 80° C. in vacuo, giving 5.4 g of the hydrazide 4. HPLC-MS: Rt=1.263 min; [M+H+]: 257.1

D)

Synthesis of (3-fluorobenzyl)-{5-[5-(1-methyl-1H-pyrazol-4-yl)-1H-pyrrolo-[2,3-b]pyridin-3-yl]-1,3,4-oxadiazol-2-yl}amine (No. 48 from Confirmation Example Table, as Example of Representative 5 from General Scheme 1)

100 mg of the hydrazide 4 prepared above and 67 mg of 3-fluorobenzyl isothiocyanate are dissolved in 5 ml of tert-butanol, then stirred at 100° C. for 10 min. and subsequently at 60° C. for 1 h. The reaction mixture is subsequently evaporated to dryness, and 5 ml of acetonitrile and 112 mg of N-(3-dimethylaminopropyl)-N'-ethylcarbodiimide hydrochloride are added. The suspension is warmed at reflux for 1.5 h.

After cooling to RT, the crystals are filtered off with suction, washed with acetonitrile and dried at 50° C. in a vacuum drying cabinet, giving 114 mg of the title compound as colourless solid. (analysis see table)

E)

Synthesis of ((2-chlorophenyl)-{5-[5-(1-methyl-1H-pyrazol-4-yl)-1H-pyrrolo-[2,3-b]pyridin-3-yl]-1,3,4-oxadiazol-2-yl}amino)acetonitrile (No. 49 from Confirmation Example Table)

a) Synthesis of {5-[1-benzenesulfonyl-5-(1-methyl-1H-pyrazol-4-yl)-1H-pyrrolo-[2,3-b]pyridin-3-yl]-1,3,4-oxadiazol-2-yl}-2-chlorophenyl)amine (as example of substance 6 from General Scheme 1)

1.3 g of (2-chlorophenyl)-{5-[5-(1-methyl-1H-pyrazol-4-yl)-1H-pyrrolo[2,3-b]-pyridin-3-yl]-1,3,4-oxadiazol-2-yl}amine are dissolved in 15 ml of DMF at 60° C. When the solution has re-cooled to RT, 1.4 ml of triethylamine and 40 mg of dimethylaminopyridine are added. This solution is then cooled to 0° C., before 0.5 ml of benzenesulfonyl chloride is added dropwise. When the addition is complete, the batch is stirred at RT for a further 4 h. After undissolved constituents have been filtered off, the solution which remains is evaporated completely to dryness, and the residue is partitioned between ethyl acetate and water, with crystals precipitating out after a short time. The product is filtered off with suction and combined with the second crystal batch, giving 1.3 g of the title compound. HPLC-MS: Rt=2.567 min; [M+H+]: 532.1 b) Synthesis of [{5-[1-benzenesulfonyl-5-(1-methyl-1H-pyrazol-4-yl)-1H-pyrrolo[2,3-b]pyridin-3-yl]-1,3,4-oxadiazol-2-yl}-(2-chlorophenyl)amino]-acetonitrile 250 mg of the {5-[1-benzenesulfonyl-5-(1-methyl-1H-pyrazol-4-yl)-1H-pyrrolo-[2,3-b]pyridin-3-yl]-1,3,4-oxadiazol-2-yl}-2-chlorophenyl)amine prepared above under a), 400 mg of iodoacetonitrile and 400 μl of N-ethyldiisopropylamine are combined in 5 ml of DMF, and the reaction mixture is warmed at 100° C. for 2 h. After cooling to RT, the batch is partitioned between ethyl acetate/water, the aqueous phase is extracted to exhaustion, the combined organic phase is dried and evaporated. The residue is purified by chromatography on silica gel with ethyl acetate, giving 230 mg of the amorphous product. HPLC-MS: Rt=2.442 min; [M+H+]: 571.1 c) 230 mg of the [{5-[1-benzenesulfonyl-5-(1-methyl-1H-pyrazol-4-yl)-1H-pyrrolo[2,3-b]pyridin-3-yl]-1,3,4-oxadiazol-2-yl}-(2-chlorophenyl)amino]-acetonitrile prepared above under b) are dissolved in 5 ml of methanol, and 80 mg of potassium carbonate are added. This mixture is stirred at 50° C. for 1 h. The solvent is subsequently removed in vacuo, and the residue is partitioned between ethyl acetate and water. After exhaustive extraction of the aqueous phase, the combined organic phases are dried and evaporated. The residue is dissolved in a little methanol, and the crystallising product is filtered off with suction, giving 60 mg of the product as beige crystals. (analysis see table)

F)

a) Synthesis of methyl 3-chloro-4-{5-[5-(1-methyl-1H-pyrazol-4-yl)-1H-pyrrolo-[2,3-b]pyridin-3-yl]-1,3,4-oxadiazol-2-ylamino}benzoate (No. 18 from table)

Analogously to D), 280 mg of the title compound (analysis see table) are obtained from 190 mg of the hydrazide and 170 mg of the isothiocyanate b) Synthesis of 3-chloro-N-cyclohexyl-4-{5-[5-(1-methyl-1H-pyrazol-4-yl)-1H-pyrrolo[2,3-b]pyridin-3-yl]-1,3,4-oxadiazol-2-ylamino}benzamide (No. 66 from table)

1.8 g of the ester prepared above are dissolved in 30 ml of methanol, and 2 ml of 32% sodium hydroxide solution are added. The reaction mixture is stirred at 50° C. for 4 h. When the reaction is complete, the batch is adjusted to pH=3 using 37% HCl, and the precipitating crystals are filtered off with suction. Drying at 80° C. in vacuo gives 1.6 g of the corresponding acid.

c) 100 mg of the acid prepared above and 115 mg of cyclohexylamine are combined in 3 ml of T3P. This mixture is stirred in a sealed vessel at 80° C. for 1 h. Liquid constituents are removed in vacuo, and the residue is purified by preparative HPLC, giving 20 mg of the product as colourless solid (analysis see Table 1).

The following compounds are obtained analogously:

TABLE 1

| No. | Structure and/or name | $^1$H NMR (400 MHz, DMSO-$d_6$); J [Hz]; δ [ppm] | LC-MS; rt; [M + H]$^+$ |
|---|---|---|---|
| 1 | (4-Fluorobenzyl)-{5-[5-(1-methyl-1H-pyrazol-4-yl)-1H-pyrrolo[2,3-b]-pyridin-3-yl]-1,3,4-oxadiazol-2-yl}-amine | 12.31 (d, J = 2.3, 1H), 8.61 (d, J = 2.1, 1H), 8.40 (d, J = 2.1, 1H), 8.21 (s, 1H), 8.13 (t, J = 6.2, 1H), 7.99 (d, J = 2.8, 1H), 7.91 (d, J = 0.5, 1H), 7.55-7.37 (m, 2H), 7.29-7.09 (m, 2H), 4.45 (d, J = 6.1, 2H), 3.90 (s, 3H) | 1.919 min [390.1] |
| 2 | N-{5-[5-(1-Methyl-1H-pyrazol-4-yl)-1H-pyrrolo[2,3-b]pyridin-3-yl]-1,3,4-oxadiazol-2-yl}benzamide | 12.41 (d, J = 2.5, 1H), 10.49 (s, 1H), 8.63 (d, J = 2.1, 1H), 8.48 (d, J = 2.1, 1H), 8.24 (s, 1H), 8.05 (d, J = 2.9, 1H), 7.94 (s, 1H), 6.88 (d, J = 2.2, 2H), 6.19 (t, J = 2.2, 1H), 3.91 (s, 3H). | 2.027 min [418.1] |
| 3 | 3-{5-[5-(1-Methyl-1H-pyrazol-4-yl)-1H-pyrrolo[2,3-b]pyridin-3-yl]-1,3,4-oxadiazol-2-ylamino}benzonitrile | 12.47 (d, J = 2.3, 1H), 11.01 (s, 1H), 8.69-8.61 (m, 1H), 8.47 (t, J = 13.1, 1H), 8.26 (s, 1H), 8.11 (dd, J = 4.9, 2.4, 2H), 7.95 (s, 1H), 7.91 (dt, J = 8.3, 4.2, 1H), 7.61 (t, J = 8.0, 1H), 7.48 (d, J = 7.6, 1H), 3.92 (s, 3H). | 1.983 min [383.1] |

TABLE 1-continued

| No. | Structure and/or name | ¹H NMR (400 MHz, DMSO-d₆); J [Hz]; δ [ppm] | LC-MS; rt; [M + H]⁺ |
|---|---|---|---|
| 21 | 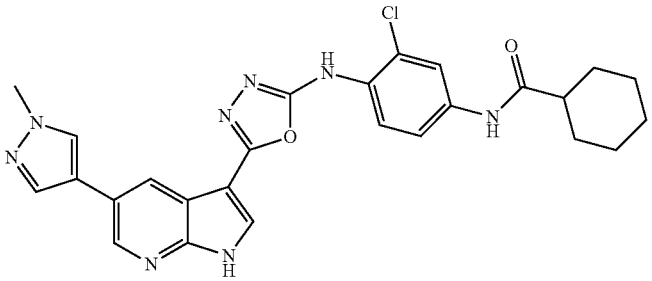 [SMILES: Cn1cc(-c2cnc3[nH]cc(-c4nnc(Nc5ccc(NC(=O)C6CCCCC6)cc5Cl)o4)c3c2)cn1]<br>N-(3-Chloro-4-{5-[5-(1-methyl-1H-pyrazol-4-yl)-1H-pyrrolo[2,3-b]-pyridin-3-yl]-1,3,4-oxadiazol-2-ylamino}phenyl)cyclohexane-carboxamide | 12.40 (s, 1H), 9.95 (s, 1H), 9.73 (s, 1H), 8.62 (d, J = 2.1, 1H), 8.45 (d, J = 2.1, 1H), 8.22 (s, 1H), 8.06 (s, 1H), 7.94 (d, J = 2.3, 1H), 7.91 (d, J = 8.1, 2H), 7.50 (dd, J = 8.9, 2.4, 1H), 3.90 (s, 3H), 2.39-2.28 (m, 1H), 1.86-1.73 (m, 4H), 1.66 (d, J = 11.8, 1H), 1.42 (qd, J = 12.2, 2.5, 2H), 1.34-1.14 (m, 3H). | 2.173 min [517.2] |
| 22 | 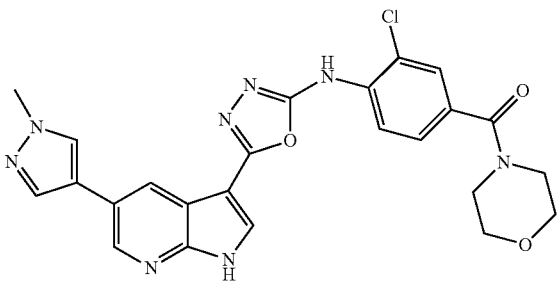 [SMILES: Cn1cc(-c2cnc3[nH]cc(-c4nnc(Nc5ccc(C(=O)N6CCOCC6)cc5Cl)o4)c3c2)cn1]<br>(3-Chloro-4-{5-[5-(1-methyl-1H-pyrazol-4-yl)-1H-pyrrolo[2,3-b]-pyridin-3-yl]-1,3,4-oxadiazol-2-ylamino}phenyl)morpholin-4-ylmethanone | 12.45 (d, J = 2.0, 1H), 10.05 (s, 1H), 8.65 (d, J = 2.1, 1H), 8.51 (d, J = 2.0, 1H), 8.26 (d, J = 1.8, 1H), 8.24 (s, 1H), 8.11 (d, J = 2.7, 1H), 7.95 (s, 1H), 7.61 (d, J = 8.1, 1H), 7.17 (dd, J = 8.1, 1.9, 1H), 3.92 (s, 3H), 3.74-3.39 (m, 8H) | 1.829 min [505.1] |
| 23 | 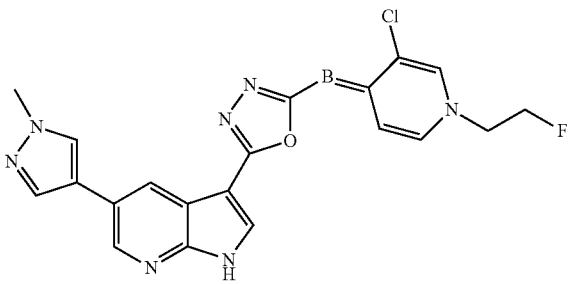 [SMILES: Cn1cc(-c2cnc3[nH]cc(-c4nnc(/B=C5\C=CN(CCF)C=C5Cl)o4)c3c2)cn1]<br>[3-Chloro-1-(2-fluoroethyl)-1H-pyridin-(4E)-ylidene]-{5-[5-(1-methyl-1H-pyrazol-4-yl)-1H-pyrrolo-[2,3-b]pyridin-3-yl]-1,3,4-oxadiazol-2-yl}amine | 12.32 (s, 1H), 8.61 (d, J = 2.1, 1H), 8.50 (d, J = 2.1, 1H), 8.38 (d, J = 1.7, 1H), 8.24 (s, 1H), 8.16 (s, 1H), 8.11 (d, J = 7.5, 1H), 8.01 (dd, J = 7.5, 1.7, 1H), 7.91 (s, 1H), 4.80 (dt, J = 47.1, 4.5, 2H), 4.39 (dt, J = 27.2, 4.6, 2H), 3.91 (s, 3H) | 1.540 min [439.1] |

TABLE 1-continued

| No. | Structure and/or name | ¹H NMR (400 MHz, DMSO-d₆); J [Hz]; δ [ppm] | LC-MS; rt; [M + H]⁺ |
|---|---|---|---|
| 24 | 3-Chloro-N-(1-methyl-1H-pyrazol-4-yl)-4-{5-[5-(1-methyl-1H-pyrazol-4-yl)-1H-pyrrolo[2,3-b]pyridin-3-yl]-1,3,4-oxadiazol-2-ylamino}benzamide | 12.45 (d, J = 1.9, 1H), 10.50 (s, 1H), 8.68 (s, 1H), 8.65 (d, J = 2.1, 1H), 8.51 (d, J = 2.0, 1H), 8.24 (s, 1H), 8.16 (s, 0H), 8.11 (d, J = 2.7, 1H), 8.03 (s, 1H), 7.95 (d, J = 0.5, 1H), 7.70 (d, J = 1.0, 2H), 7.59 (s, 1H), 3.91 (s, 3H), 3.84 (s, 3H). | 1.891 min [515.1] |
| 25 | N-Carbamoylmethyl-3-chloro-4-{5-[5-(1-methyl-1H-pyrazol-4-yl)-1H-pyrrolo[2,3-b]pyridin-3-yl]-1,3,4-oxadiazol-2-ylamino}benzamide | 12.43 (d, J = 1.8, 1H), 9.98 (s, 1H), 8.70 (t, J = 5.8, 1H), 8.63 (d, J = 2.1, 1H), 8.60 (s, 1H), 8.49 (d, J = 1.6, 1H), 8.23 (s, 1H), 8.09 (d, J = 2.6, 1H), 7.94 (s, 1H), 7.63 (d, J = 8.0, 2H), 7.38 (s, 1H), 7.02 (s, 1H), 3.90 (s, 3H), 3.83 (d, J = 5.8, 2H). | 1.701 min [492.1] |
| 26 | 3-Chloro-N-(1-hydroxymethylpropyl)-4-{5-[5-(1-methyl-1H-pyrazol-4-yl)-1H-pyrrolo[2,3-b]pyridin-3-yl]-1,3,4-oxadiazol-2-ylamino}benzamide | 12.43 (s, 1H), 9.97 (s, 1H), 8.63 (d, J = 2.1, 1H), 8.56 (s, 1H), 8.49 (d, J = 1.6, 1H), 8.23 (s, 1H), 8.08 (t, J = 6.1, 2H), 7.94 (d, J = 8.6, 2H), 7.62 (s, 2H), 4.66 (t, J = 5.7, 1H), 3.94-3.82 (m, 4H), 3.47 (m, 1H), 3.40 (m, 2H), 2.88 (m, 2H), 2.73 (m, 2H), 1.73-1.58 (m, 1H), 1.51-1.39 (m, 1H), 0.87 (t, J = 7.4, 3H) | 1.822 min [507.1] |
| 27 | 3-Chloro-N-cyclopropylmethyl-4-{5-[5-(1-methyl-1H-pyrazol-4-yl)-1H-pyrrolo[2,3-b]pyridin-3-yl]-1,3,4-oxadiazol-2-ylamino}benzamide | 12.21 (d, J = 2.3, 1H), 9.74 (s, 1H), 8.41 (d, J = 2.1, 1H), 8.39 (d, J = 5.7, 1H), 8.35 (s, 1H), 8.26 (d, J = 1.5, 1H), 8.00 (s, 1H), 7.87 (d, J = 2.8, 1H), 7.71 (s, 1H), 7.40 (d, J = 8.3, 1H), 7.37 (dd, J = 8.3, 1.8, 1H), 3.67 (d, J = 6.5, 3H), 2.97-2.89 (m, 2H), 0.87-0.74 (m, 1H), 0.24-0.18 (m, 2H), 0.04--0.02 (m, 2H). | 1.968 min [489.1] |

TABLE 1-continued

| No. | Structure and/or name | $^1$H NMR (400 MHz, DMSO-d$_6$); J [Hz]; δ [ppm] | LC-MS; rt; [M + H]$^+$ |
|---|---|---|---|
| 28 | 3-Chloro-N-(2-fluoroethyl)-4-{5-[5-(1-methyl-1H-pyrazol-4-yl)-1H-pyrrolo[2,3-b]pyridin-3-yl]-1,3,4-oxadiazol-2-ylamino}benzamide | 12.40 (d, J = 46.8, 1H), 9.99 (s, 1H), 8.78 (t, J = 5.5, 1H), 8.65 (d, J = 2.1, 1H), 8.61 (s, 1H), 8.50 (d, J = 1.9, 1H), 8.24 (s, 1H), 8.10 (d, J = 2.3, 1H), 7.94 (d, J = 0.6, 1H), 7.65 (d, J = 8.3, 1H), 7.62 (dd, J = 8.3, 1.9, 1H), 4.60 (t, J = 5.1, 1H), 4.51 (t, J = 5.1, 1H), 3.92 (s, 3H), 3.61 (q, J = 5.2, 1H), 3.56 (q, J = 5.2, 1H). | 1.858 min [481.1] |
| 29 | {5-[5-(1-Methyl-1H-pyrazol-4-yl)-1H-pyrrolo[2,3-b]pyridin-3-yl]-1,3,4-oxadiazol-2-yl}-(2-methylpyridin-3-yl)amine | 12.43 (d, J = 2.3, 1H), 9.76 (s, 1H), 8.64 (d, J = 2.1, 1H), 8.47 (d, J = 2.0, 1H), 8.29 (d, J = 1.3, 0H), 8.27 (d, J = 1.3, 1H), 8.24 (s, 1H), 8.21 (dd, J = 4.7, 1.4, 1H), 8.08 (d, J = 2.9, 1H), 7.93 (d, J = 0.6, 1H), 7.31 (dd, J = 8.1, 4.7, 1H), 3.92 (s, 3H), 2.57 (s, 3H). | 1.454 min [373.1] |
| 30 | 3-Chloro-N-cyclopropyl-4-{5-[5-(1-methyl-1H-pyrazol-4-yl)-1H-pyrrolo-[2,3-b]pyridin-3-yl]-1,3,4-oxadiazol-2-ylamino}benzamide | 12.43 (d, J = 2.3, 1H), 9.76 (s, 1H), 8.64 (d, J = 2.1, 1H), 8.47 (d, J = 2.0, 1H), 8.29 (d, J = 1.3, 0H), 8.27 (d, J = 1.3, 1H), 8.24 (s, 1H), 8.21 (dd, J = 4.7, 1.4, 1H), 8.08 (d, J = 2.9, 1H), 7.93 (d, J = 0.6, 1H), 7.31 (dd, J = 8.1, 4.7, 1H), 3.92 (s, 3H), 2.57 (m, 5H). | 1.882 min [475.1] |
| 31 | 3-Chloro-N-(2-dimethylaminoethyl)-4-{5-[5-(1-methyl-1H-pyrazol-4-yl)-1H-pyrrolo[2,3-b]pyridin-3-yl]-1,3,4-oxadiazol-2-ylamino}benzamide | 12.46 (d, J = 2.5, 1H), 10.02 (s, 1H), 9.87 (s, 1H), 8.85 (t, J = 5.4, 1H), 8.64 (d, J = 2.0, 2H), 8.49 (d, J = 1.6, 1H), 8.23 (s, 1H), 8.10 (d, J = 2.9, 1H), 7.94 (d, J = 8.3, 1H), 7.67 (d, J = 7.8, 2H), 3.91 (s, 3H), 3.63 (q, J = 5.9, 2H), 3.26 (m, 1H), 3.17 (m, 1H), 2.83 (s, 6H). | 1.587 min [506.1] |

TABLE 1-continued

| No. | Structure and/or name | $^1$H NMR (400 MHz, DMSO-$d_6$); J [Hz]; δ [ppm] | LC-MS; rt; [M + H]$^+$ |
|---|---|---|---|
| 32 | 3-Chloro-N-(2-methoxyethyl)-4-{5-[5-(1-methyl-1H-pyrazol-4-yl)-1H-pyrrolo[2,3-b]pyridin-3-yl]-1,3,4-oxadiazol-2-ylamino}benzamide | 12.47 (t, J = 24.0, 1H), 10.09-9.82 (m, 1H), 8.64 (d, J = 2.1, 1H), 8.58 (dd, J = 8.8, 3.4, 2H), 8.49 (d, J = 1.8, 1H), 8.22 (s, 1H), 8.10 (d, J = 2.9, 1H), 7.93 (s, 1H), 7.63 (d, J = 8.3, 1H), 7.59 (dd, J = 8.3, 1.8, 1H), 3.90 (s, 3H), 3.50-3.39 (m, 4H), 3.27 (s, 3H). | 1.846 min [493.1] |
| 33 | 3-Chloro-N-diethylcarbamoylmethyl-4-{5-[5-(1-methyl-1H-pyrazol-4-yl)-1H-pyrrolo[2,3-b]pyridin-3-yl]-1,3,4-oxadiazol-2-ylamino}benzamide | 8.63 (d, J = 2.1, 1H), 8.62-8.56 (m, 2H), 8.49 (d, J = 2.1, 1H), 8.23 (s, 1H), 8.18 (s, 0H), 8.10 (s, 1H), 7.94 (d, J = 0.6, 1H), 7.65 (d, J = 8.3, 1H), 7.62 (dd, J = 8.3, 1.9, 1H), 4.11 (d, J = 5.6, 2H), 3.90 (s, 3H), 3.46-3.30 (m, 4H), 1.17 (t, J = 7.1, 3H), 1.04 (t, J = 7.1, 3H). | 1.919 min [548.2] |
| 34 | (2-Chloropyridin-3-yl)-(2-fluoroethyl)-{5-[5-(1-methyl-1H-pyrazol-4-yl)-1H-pyrrolo[2,3-b]pyridin-3-yl]-1,3,4-oxadiazol-2-yl}-amine | 12.42 (t, J = 23.8, 1H), 8.59 (d, J = 2.1, 1H), 8.51 (dd, J = 4.7, 1.7, 1H), 8.21 (dd, J = 7.8, 1.7, 1H), 8.17 (d, J = 2.1, 1H), 8.13 (s, 1H), 8.03 (d, J = 2.8, 1H), 7.82 (d, J = 0.6, 1H), 7.65 (dd, J = 7.8, 4.7, 1H), 4.82 (t, J = 4.7, 1H), 4.72 (t, J = 4.7, 1H), 4.25 (t, J = 4.6, 1H), 4.20 (t, J = 4.6, 1H), 3.91 (s, 3H). | 1.791 min [439.1] |

TABLE 1-continued

| No. | Structure and/or name | ¹H NMR (400 MHz, DMSO-d₆); J [Hz]; δ [ppm] | LC-MS; rt; [M + H]⁺ |
|---|---|---|---|
| 35 | (2-Fluoroethyl)-{5-[5-(1-methyl-1H-pyrazol-4-yl)-1H-pyrrolo[2,3-b]-pyridin-3-yl]-1,3,4-oxadiazol-2-yl}-(2-methylpyridin-3-yl)amine | 12.39 (s, 1H), 8.59 (d, J = 2.1, 1H), 8.53 (dd, J = 4.7, 1.5, 1H), 8.14 (d, J = 2.1, 2H), 8.04 (d, J = 2.1, 1H), 7.92 (dd, J = 8.0, 1.4, 1H), 7.83 (d, J = 0.5, 1H), 7.42 (dd, J = 7.9, 4.8, 1H), 4.79 (t, J = 4.6, 1H), 4.67 (t, J = 4.7, 1H), 4.23 (t, J = 4.7, 1H), 4.16 (t, J = 4.6, 1H), 3.91 (s, 3H), 2.45 (s, 3H). | 1.642 min [419.1] |
| 36 | 3-Chloro-N-methylcarbamoylmethyl-4-{5-[5-(1-methyl-1H-pyrazol-4-yl)-1H-pyrrolo[2,3-b]pyridin-3-yl]-1,3,4-oxadiazol-2-ylamino}benzamide | 12.43 (d, J = 2.3, 1H), 10.01 (s, 1H), 8.78 (t, J = 5.9, 1H), 8.64 (d, J = 2.1, 1H), 8.61 (d, J = 1.0, 1H), 8.50 (d, J = 1.9, 1H), 8.23 (s, 1H), 8.11 (d, J = 2.9, 1H), 7.94 (s, 1H), 7.87-7.80 (m, 1H), 7.67-7.61 (m, 2H), 3.90 (d, J = 5.6, 3H), 3.84 (d, J = 5.8, 2H), 2.61 (d, J = 4.6, 3H). | 1.733 min [506.1] |
| 37 | N-(3-Chloro-4-{5-[5-(1-methyl-1H-pyrazol-4-yl)-1H-pyrrolo[2,3-b]-pyridin-3-yl]-1,3,4-oxadiazol-2-ylamino}phenyl)acetamide | 12.38 (s, 1H), 10.07 (s, 1H), 9.70 (s, 1H), 8.61 (d, J = 2.1, 1H), 8.45 (d, J = 2.0, 1H), 8.20 (s, 1H), 8.05 (d, J = 2.8, 1H), 7.92 (d, J = 10.0, 3H), 7.46 (dd, J = 8.9, 2.2, 1H), 3.90 (s, 2H), 2.06 (s, 3H). | 1.711 min [407.1] |
| 38 | N-(3-Chloro-4-{5-[5-(1-methyl-1H-pyrazol-4-yl)-1H-pyrrolo[2,3-b]-pyridin-3-yl]-1,3,4-oxadiazol-2-ylamino}phenyl)-2-methylacrylamide | 12.37 (s, 1H), 9.91 (s, 1H), 9.76 (s, 1H), 8.62 (d, J = 2.1, 1H), 8.46 (d, J = 2.1, 1H), 8.22 (s, 1H), 8.07 (d, J = 2.6, 1H), 7.98 (d, J = 2.3, 1H), 7.95 (s, 1H), 7.92 (s, 1H), 7.67 (dd, J = 8.9, 2.4, 1H), 5.84 (s, 1H), 5.55 (s, 1H), 3.91 (d, J = 4.1, 3H), 1.96 (s, 3H). | 1.976 min [475.1] |

TABLE 1-continued

| No. | Structure and/or name | ¹H NMR (400 MHz, DMSO-d₆); J [Hz]; δ [ppm] | LC-MS; rt; [M + H]⁺ |
|---|---|---|---|
| 39 | 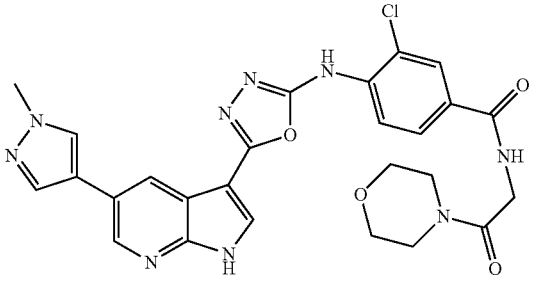 [SMILES: Cn1cc(-c2cnc3[nH]cc(-c4nnc(Nc5ccc(C(=O)NCC(=O)N6CCOCC6)cc5Cl)o4)c3c2)cn1]<br>3-Chloro-4-{5-[5-(1-methyl-1H-pyrazol-4-yl)-1H-pyrrolo[2,3-b]-pyridin-3-yl]-1,3,4-oxadiazol-2-ylamino}-N-(2-morpholin-4-yl-2-oxoethyl)benzamide | 12.43 (s, 1H), 9.98 (s, 1H), 8.63 (d, J = 2.1, 1H), 8.61 (d, J = 5.6, 2H), 8.49 (d, J = 1.7, 1H), 8.23 (s, 1H), 8.09 (d, J = 2.6, 1H), 7.93 (d, J = 0.6, 1H), 7.65 (d, J = 8.3, 1H), 7.61 (dd, J = 8.3, 1.8, 1H), 4.14 (d, J = 5.6, 2H), 3.90 (s, 3H), 3.59 (d, J = 10.5, 4H), 3.49 (d, J = 11.6, 4H). | 1.859 min [562.2] |
| 40 | 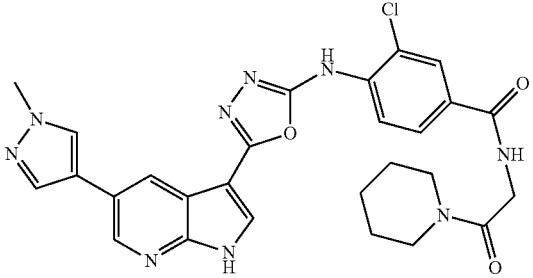 [SMILES: Cn1cc(-c2cnc3[nH]cc(-c4nnc(Nc5ccc(C(=O)NCC(=O)N6CCCCC6)cc5Cl)o4)c3c2)cn1]<br>3-Chloro-4-{5-[5-(1-methyl-1H-pyrazol-4-yl)-1H-pyrrolo[2,3-b]-pyridin-3-yl]-1,3,4-oxadiazol-2-ylamino}-N-(2-oxo-2-piperidin-1-ylethyl)benzamide | 12.43 (s, 1H), 9.98 (s, 1H), 8.63 (d, J = 2.1, 1H), 8.58 (d, J = 9.3, 1H), 8.55 (t, J = 5.5, 1H), 8.49 (d, J = 2.1, 1H), 8.23 (s, 1H), 8.09 (s, 1H), 7.93 (d, J = 0.6, 1H), 7.65 (d, J = 8.3, 1H), 7.61 (dd, J = 8.3, 1.9, 1H), 4.12 (d, J = 5.6, 2H), 3.90 (s, 3H), 3.44 (d, J = 4.4, 4H), 1.54 (m, 6H). | 1.953 min [561.1] |
| 41 | 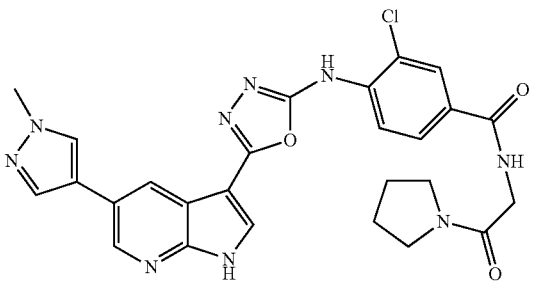 [SMILES: Cn1cc(-c2cnc3[nH]cc(-c4nnc(Nc5ccc(C(=O)NCC(=O)N6CCCC6)cc5Cl)o4)c3c2)cn1]<br>3-Chloro-4-{5-[5-(1-methyl-1H-pyrazol-4-yl)-1H-pyrrolo[2,3-b]-pyridin-3-yl]-1,3,4-oxadiazol-2-ylamino}-N-(2-oxo-2-pyrrolidin-1-ylethyl)benzamide | 12.43 (s, 1H), 10.01 (s, 1H), 8.63 (d, J = 2.1, 1H), 8.62 (d, J = 5.7, 2H), 8.50 (d, J = 2.0, 1H), 8.23 (s, 1H), 8.11 (d, J = 1.8, 1H), 7.94 (d, J = 0.7, 1H), 7.65 (d, J = 8.3, 1H), 7.61 (dd, J = 8.3, 1.9, 1H), 4.03 (d, J = 5.6, 2H), 3.90 (s, 3H), 3.48 (m, 4H), 1.98-1.87 (m, 2H), 1.84-1.74 (m, 2H). | 1.964 min [546.2] |

TABLE 1-continued

| No. | Structure and/or name | $^1$H NMR (400 MHz, DMSO-$d_6$); J [Hz]; δ [ppm] | LC-MS; rt; [M + H]$^+$ |
|---|---|---|---|
| 42 | 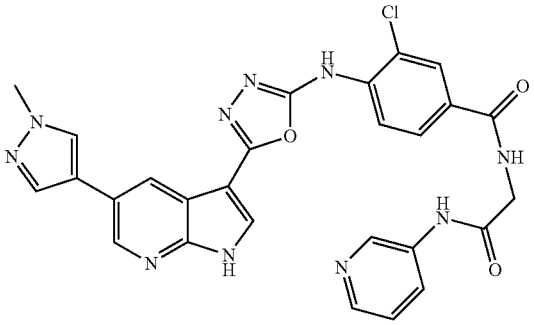 [SMILES: Cn1cc(-c2cnc3[nH]cc(-c4nnc(Nc5ccc(C(=O)NCC(=O)Nc6cccnc6)cc5Cl)o4)c3c2)cn1]<br>3-Chloro-4-{5-[5-(1-methyl-1H-pyrazol-4-yl)-1H-pyrrolo[2,3-b]-pyridin-3-yl]-1,3,4-oxadiazol-2-ylamino}-N-(pyridin-3-yl-carbamoylmethyl)benzamide | 12.43 (s, 1H), 10.28 (s, 1H), 8.93 (t, J = 5.8, 1H), 8.76 (d, J = 2.1, 1H), 8.63 (d, J = 2.1, 2H), 8.49 (d, J = 2.1, 1H), 8.27 (dd, J = 4.7, 1.5, 1H), 8.22 (s, 1H), 8.09 (s, 1H), 8.04 (ddd, J = 8.4, 2.5, 1.5, 1H), 7.93 (d, J = 0.7, 1H), 7.69-7.62 (m, 2H), 7.35 (dd, J = 8.1, 4.5, 1H), 4.11 (d, J = 5.8, 2H), 3.90 (s, 3H). | 1.821 min [569.1] |
| 43 | 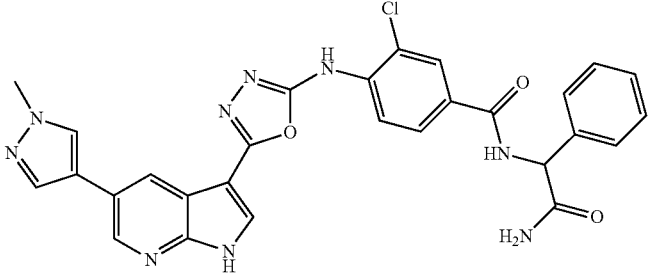 [SMILES: Cn1cc(-c2cnc3[nH]cc(-c4nnc(Nc5ccc(C(=O)NC(C(N)=O)c6ccccc6)cc5Cl)o4)c3c2)cn1]<br>N-(Carbamoylphenylmethyl)-3-chloro-4-{5-[5-(1-methyl-1H-pyrazol-4-yl)-1H-pyrrolo[2,3-b]pyridin-3-yl]-1,3,4-oxadiazol-2-ylamino}benzamide | 12.42 (s, 1H), 9.98 (s, 1H), 8.77 (d, J = 7.9, 1H), 8.63 (d, J = 2.1, 1H), 8.61 (d, J = 1.8, 1H), 8.49 (d, J = 2.0, 1H), 8.23 (s, 1H), 8.09 (d, J = 2.6, 1H), 7.93 (s, 1H), 7.69 (s, 1H), 7.67 (d, J = 1.8, 1H), 7.62 (d, J = 8.3, 1H) 7.51 (d, J = 7.1, 2H), 7.31 (ddd, J = 10.9, 9.7, 5.7, 3H), 7.22 (s, 1H), 5.63 (d, J = 7.8, 1H), 3.90 (s, 3H). | 1.995 min [568.1] |
| 44 | 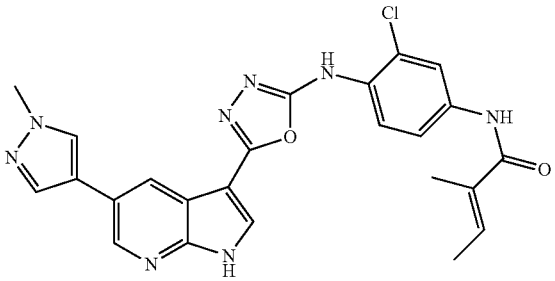 [SMILES: C/C=C(\C)C(=O)Nc1ccc(Nc2nnc(-c3c[nH]c4ncc(-c5cnn(C)c5)cc34)o2)c(Cl)c1]<br>N-(3-Chloro-4-{5-[5-(1-methyl-1H-pyrazol-4-yl)-1H-pyrrolo[2,3-b]-pyridin-3-yl]-1,3,4-oxadiazol-2-ylamino}phenyl)-(E)-2-methylbut-2-enamide | 12.40 (s, 1H), 9.77 (s, 1H), 9.73 (s, 1H), 8.62 (d, J = 2.1, 1H), 8.45 (d, J = 2.1, 1H), 8.22 (s, 1H), 8.06 (d, J = 2.7, 1H), 7.97 (d, J = 2.4, 1H), 7.92 (t, J = 4.7, 2H), 7.64 (dd, J = 8.9, 2.4, 1H), 6.67-6.26 (m, 1H), 3.90 (s, 3H), 1.88-1.83 (m, 3H), 1.79 (dd, J = 6.9, 1.1, 3H). | 2.095 min [489.1] |

TABLE 1-continued

| No. | Structure and/or name | ¹H NMR (400 MHz, DMSO-d₆); J [Hz]; δ [ppm] | LC-MS; rt; [M + H]⁺ |
|---|---|---|---|
| 45 | (2-Chlorophenyl)-(2-fluoroethyl)-{5-[5-(1-methyl-1H-pyrazol-4-yl)-1H-pyrrolo[2,3-b]pyridin-3-yl]-1,3,4-oxadiazol-2-yl}amine | 12.37 (s, 1H), 8.59 (d, J = 1.8, 1H), 8.12 (d, J = 1.9, 1H), 8.09 (s, 1H), 8.00 (s, 1H), 7.79 (s, 1H), 7.71 (dd, J = 9.0, 3.3, 2H), 7.55 (dt, J = 7.7, 3.9, 1H), 7.53-7.48 (m, 1H), 4.80 (t, J = 4.6, 1H), 4.70 (t, J = 4.6, 1H), 4.22 (t, J = 4.6, 1H), 4.17 (t, J = 4.6, 1H), 3.92 (s, 3H). | 1.974 min [438.0] |
| 46 | (2-Fluoroethyl)-(2-fluorophenyl)-{5-[5-(1-methyl-1H-pyrazol-4-yl)-1H-pyrrolo[2,3-b]pyridin-3-yl]-1,3,4-oxadiazol-2-yl}amine | 12.36 (s, 1H), 8.60 (s, 1H), 8.12 (s, 1H), 8.10 (s, 1H), 8.01 (s, 1H), 7.79 (s, 1H), 7.71 (dd, J = 9.0, 3.3, 2H), 7.55 (dt, J = 7.7, 3.9, 1H), 7.53-7.48 (m, 1H), 4.80 (t, J = 4.6, 1H), 4.70 (t, J = 4.6, 1H), 4.22 (t, J = 4.6, 1H), 4.17 (t, J = 4.6, 1H), 3.91 (s, 3H). | 1.832 min [450.0] |
| 48 | (3-Fluorobenzyl)-{5-[5-(1-methyl-1H-pyrazol-4-yl)-1H-pyrrolo[2,3-b]-pyridin-3-yl]-1,3,4-oxadiazol-2-yl}-amine | 12.31 (d, J = 2.1, 1H), 8.60 (d, J = 2.1, 1H), 8.39 (d, J = 2.1, 1H), 8.20 (s, 1H), 8.17 (t, J = 6.2, 1H), 7.99 (d, J = 2.8, 1H), 7.90 (d, J = 0.5, 1H), 7.40 (td, J = 7.9, 6.3, 1H), 7.24 (dd, J = 15.1, 5.0, 2H), 7.10 (td, J = 8.5, 2.2, 1H), 4.47 (t, J = 13.5, 2H), 3.95-3.84 (m, 3H). | 1.913 min [390.1] |
| 49 | ((2-Chlorophenyl)-{5-[5-(1-methyl-1H-pyrazol-4-yl)-1H-pyrrolo[2,3-b]-pyridin-3-yl]-1,3,4-oxadiazol-2-yl}-amino)acetonitrile | 12.44 (s, 1H), 8.61 (d, J = 2.1, 1H), 8.18 (d, J = 2.1, 1H), 8.12 (s, 1H), 8.06 (s, 1H), 7.81 (s, 1H), 7.78-7.74 (m, 2H), 7.62-7.55 (m, 2H), 5.11-5.05 (m, 2H), 3.92 (s, 3H). | 1.953 min [431.1] |

TABLE 1-continued

| No. | Structure and/or name | ¹H NMR (400 MHz, DMSO-d₆); J [Hz]; δ [ppm] | LC-MS; rt; [M + H]⁺ |
|---|---|---|---|
| 50 | (2-Chlorophenyl)methyl-{5-[5-(1-methyl-1H-pyrazol-4-yl)-1H-pyrrolo-[2,3-b]pyridin-3-yl]-1,3,4-oxadiazol-2-yl}amine | 12.36 (s, 1H), 8.59 (d, J = 2.1, 1H), 8.15 (d, J = 2.1, 1H), 8.10 (s, 1H), 7.99 (d, J = 2.2, 1H), 7.79 (d, J = 0.6, 1H), 7.72 (dd, J = 7.8, 1.6, 1H), 7.69 (dd, J = 7.9, 1.6, 1H), 7.54 (td, J = 7.6, 1.6, 1H), 7.49 (td, J = 7.7, 1.7, 1H), 3.91 (s, 3H), 3.48 (s, 3H). | 2.008 min [406.1] |
| 51 | 2-((2-Chlorophenyl)-{5-[5-(1-methyl-1H-pyrazol-4-yl)-1H-pyrrolo[2,3-b]-pyridin-3-yl]-1,3,4-oxadiazol-2-yl}-amino)acetamide | 12.51-12.20 (m, 1H), 8.58 (d, J = 2.1, 1H), 8.15 (d, J = 2.0, 1H), 8.10 (s, 1H), 8.00 (d, J = 2.9, 1H), 7.82-7.78 (m, 2H), 7.66 (dd, J = 7.9, 1.6, 1H), 7.64 (s, 1H), 7.51 (td, J = 7.7, 1.6, 1H), 7.46 (td, J = 7.7, 1.7, 1H), 7.28 (s, 1H), 4.41 (s, 2H), 3.90 (s, 3H). | 1.738 min [449.1] |
| 52 | (2,6-Dimethylphenyl)-{5-[5-(1-methyl-1H-pyrazol-4-yl)-1H-pyrrolo-[2,3-b]pyridin-3-yl]-1,3,4-oxadiazol-2-yl}amine | 12.30 (s, 1H), 9.27 (s, 1H), 8.59 (t, J = 6.1, 1H), 8.33 (d, J = 2.1, 1H), 8.16 (d, J = 8.4, 1H), 7.98 (d, J = 2.6, 1H), 7.88-7.83 (m, 1H), 7.15 (s, 3H), 3.90 (s, 3H), 2.26 (s, 6H). | 1.973 min [386.1] |

TABLE 1-continued

| No. | Structure and/or name | ¹H NMR (400 MHz, DMSO-d₆); J [Hz]; δ [ppm] | LC-MS; rt; [M + H]⁺ |
|---|---|---|---|
| 53 | 2-((2-Chlorophenyl)-{5-[5-(1-methyl-1H-pyrazol-4-yl)-1H-pyrrolo[2,3-b]-pyridin-3-yl]-1,3,4-oxadiazol-2-yl}-amino)-N-ethylacetamide | 12.37 (d, J = 2.2, 1H), 8.59 (d, J = 2.1, 1H), 8.18 (t, J = 5.5, 1H), 8.15 (d, J = 2.1, 1H), 8.11 (s, 1H), 8.00 (d, J = 2.8, 1H), 7.82-7.78 (m, 2H), 7.67 (dd, J = 7.9, 1.6, 1H), 7.52 (td, J = 7.7, 1.6, 1H), 7.47 (td, J = 7.7, 1.7, 1H), 4.42 (s, 2H), 3.91 (s, 3H), 3.17-3.10 (m, 2H), 1.02 (dd, J = 9.3, 5.2, 3H). | 1.812 min [477.1] |
| 54 | (2-Chlorophenyl)-{5-[5-(1-methyl-1H-pyrazol-4-yl)-1H-pyrrolo[2,3-b]-pyridin-3-yl]-1,3,4-oxadiazol-2-yl}-amine | 12.43 (s, 1H), 10.47-10.11 (m, 1H), 8.63 (d, J = 2.1, 1H), 8.49 (d, J = 2.0, 1H), 8.23 (s, 1H), 8.16 (td, J = 8.5, 1.4, 1H), 8.09 (d, J = 2.8, 1H), 7.94 (d, J = 0.5, 1H), 7.30 (ddd, J = 11.5, 8.2, 1.2, 1H), 7.26 (t, J = 7.8, 1H), 7.13-7.07 (m, 1H), 3.90 (s, 3H). | 2.006 min [346.1] m.p. 295-297° C. |
| 55 | Cyclohexyl-{5-[5-(1-methyl-1H-pyrazol-4-yl)-1H-pyrrolo[2,3-b]-pyridin-3-yl]-1,3,4-oxadiazol-2-yl}-amine | 12.28 (s, 1H), 8.60 (d, J = 2.1, 1H), 8.40 (d, J = 2.1, 1H), 8.20 (s, 1H), 7.95 (d, J = 2.8, 1H), 7.90 (s, 1H), 7.48 (d, J = 7.6, 1H), 3.90 (s, 3H), 2.82 (m, 1H), 2.00 (dd, J = 8.0, 4.6, 2H), 1.75 (d, J = 8.7, 2H), 1.59 (d, J = 11.9, 1H), 1.40-1.25 (m, 4H), 1.19 (m, 1H). | 1.956 min [364.2] |
| 56 | 2-((2-Chlorophenyl)-{5-[5-(1-methyl-1H-pyrazol-4-yl)-1H-pyrrolo[2,3-b]-pyridin-3-yl]-1,3,4-oxadiazol-2-yl}-amino)-N-methylacetamide | 8.58 (d, J = 2.1, 1H), 8.31 (s, 1H), 8.15 (dd, J = 7.0, 3.3, 2H), 8.10 (s, 1H), 8.00 (s, 1H), 7.81-7.78 (m, 2H), 7.67 (dd, J = 7.9, 1.6, 1H), 7.53-7.49 (m, 1H), 7.49-7.45 (m, 1H), 4.43 (s, 2H), 3.91 (s, 3H), 2.88 (d, J = 11.3, 1H), 2.73 (d, J = 0.5, 1H), 2.65 (d, J = 4.6, 3H). | 1.750 min [463.1] |

TABLE 1-continued

| No. | Structure and/or name | $^1$H NMR (400 MHz, DMSO-d$_6$); J [Hz]; δ [ppm] | LC-MS; rt; [M + H]$^+$ |
|---|---|---|---|
| 57 | 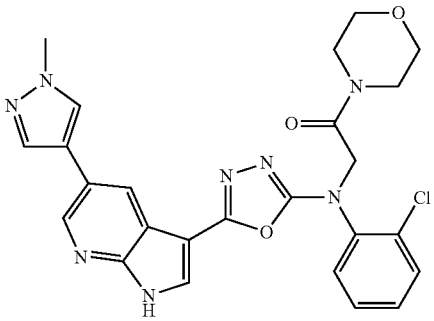 [SMILES: Cn1cc(-c2cnc3[nH]cc(-c4nnc(N(CC(=O)N5CCOCC5)c5ccccc5Cl)o4)c3c2)cn1]<br>(2-((2-Chlorophenyl)-{5-[5-(1-methyl-1H-pyrazol-4-yl)-1H-pyrrolo[2,3-b]-pyridin-3-yl]-1,3,4-oxadiazol-2-yl}-amino)-1-morpholin-4-ylethanone | 12.37 (s, 1H), 8.58 (d, J = 2.1, 1H), 8.15 (d, J = 2.1, 1H), 8.11 (s, 1H), 8.00 (s, 1H), 7.80 (d, J = 0.5, 1H), 7.77 (dd, J = 7.8, 1.7, 1H), 7.67 (dd, J = 7.9, 1.6, 1H), 7.50 (td, J = 7.7, 1.6, 1H), 7.46 (td, J = 7.7, 1.7, 1H), 4.81 (s, 2H), 3.91 (s, 3H), 3.61 (m, 2H), 3.56 (m, 2H), 3.51 (m, 2H), 3.47 (m, 2H). | 1.828 min [519.1] |
| 58 | 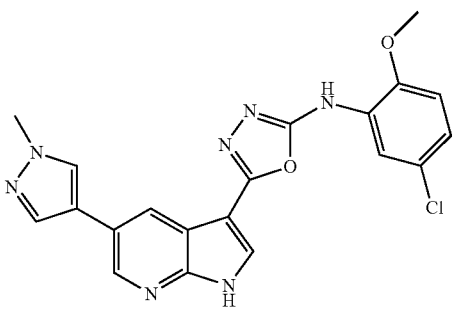 [SMILES: COc1ccc(Cl)cc1Nc1nnc(-c2c[nH]c3ncc(-c4cnn(C)c4)cc23)o1]<br>(5-Chloro-2-methoxyphenyl)-{5-[5-(1-methyl-1H-pyrazol-4-yl)-1H-pyrrolo[2,3-b]pyridin-3-yl]-1,3,4-oxadiazol-2-yl}amine | 12.43 (d, J = 2.3, 1H), 9.87 (s, 1H), 8.63 (d, J = 2.1, 1H), 8.53 (d, J = 2.1, 1H), 8.26 (d, J = 2.3, 1H), 8.24 (s, 1H), 8.09 (d, J = 2.8, 1H), 7.96 (d, J = 0.7, 1H), 7.10 (d, J = 8.7, 1H), 7.07 (dd, J = 8.7, 2.3, 1H), 3.91 (s, 3H), 3.91 (s, 3H). | 2.219 min [422.1] |
| 59 | 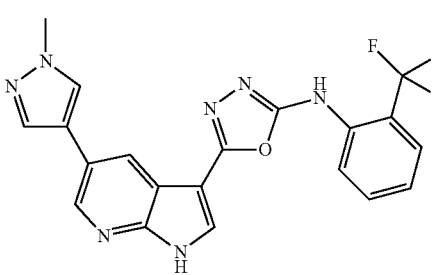<br>{5-[5-(1-Methyl-1H-pyrazol-4-yl)-1H-pyrrolo[2,3-b]pyridin-3-yl]-1,3,4-oxadiazol-2-yl}-(2-trifluoromethylphenyl)amine | 12.40 (s, 1H), 9.68 (s, 1H), 8.62 (d, J = 2.1, 1H), 8.41 (s, 1H), 8.20 (s, 1H), 8.06 (d, J = 2.3, 1H), 7.96 (d, J = 7.9, 1H), 7.89 (s, 1H), 7.76 (dd, J = 16.6, 7.9, 2H), 7.42 (t, J = 7.5, 1H), 3.90 (s, 3H). | 2.076 min [426.1] |

TABLE 1-continued

| No. | Structure and/or name | ¹H NMR (400 MHz, DMSO-d₆); J [Hz]; δ [ppm] | LC-MS; rt; [M + H]⁺ |
|---|---|---|---|
| 60 | (2-Fluorophenyl)-5-[5-(1-methyl-1H-pyrazol-4-yl)-1H-pyrrolo[2,3-b]-pyridin-3-yl]-1,3,4-oxadiazol-2-yl}-amine | 12.43 (d, J = 2.0, 1H), 10.31 (s, 1H), 8.63 (d, J = 2.1, 1H), 8.49 (d, J = 2.0, 1H), 8.23 (s, 1H), 8.16 (td, J = 8.5, 1.4, 1H), 8.09 (d, J = 2.8, 1H), 7.94 (d, J = 0.5, 1H), 7.30 (ddd, J = 11.5, 8.2, 1.2, 1H), 7.26 (t, J = 7.8, 1H), 7.13-7.06 (m, 1H), 3.91 (s, 3H). | 2.006 min [376.1] m.p. 295-297° C. |
| 61 | 2-((2-Chlorophenyl)-{5-[5-(1-methyl-1H-pyrazol-4-yl)-1H-pyrrolo[2,3-b]-pyridin-3-yl]-1,3,4-oxadiazol-2-yl}-amino)-N,N-dimethylacetamide | 12.37 (s, 1H), 8.58 (d, J = 2.1, 1H), 8.14 (d, J = 2.1, 1H), 8.10 (s, 1H), 8.01 (s, 1H), 7.79 (s, 1H), 7.78 (dd, J = 7.9, 1.7, 1H), 7.66 (dd, J = 7.9, 1.6, 1H), 7.49 (td, J = 7.6, 1.6, 1H), 7.45 (td, J = 7.7, 1.8, 1H), 4.76 (s, 2H), 3.91 (s, 3H), 3.03 (s, 3H), 2.87 (s, 3H). | 1.849 min [477.1] |
| 62 | (2-Ethoxyphenyl)-{5-[5-(1-methyl-1H-pyrazol-4-yl)-1H-pyrrolo[2,3-b]-pyridin-3-yl]-1,3,4-oxadiazol-2-yl}-amine | 12.40 (d, J = 2.2, 1H), 9.36 (s, 1H), 8.64 (d, J = 2.1, 1H), 8.51 (d, J = 2.1, 1H), 8.25 (s, 1H), 8.10-8.04 (m, 2H), 7.95 (s, 1H), 7.04 (ttd, J = 14.8, 7.6, 1.8, 3H), 4.16 (q, J = 7.0, 2H), 3.92 (s, 3H), 1.41 (t, J = 7.0, 3H). | 2.132 min [402.1] m.p. 274-275° C. |
| 63 | (2-Methoxybenzyl)-{5-[5-(1-methyl-1H-pyrazol-4-yl)-1H-pyrrolo[2,3-b]-pyridin-3-yl]-1,3,4-oxadiazol-2-yl}-amine | 12.31 (s, 1H), 8.60 (d, J = 2.0, 1H), 8.41 (d, J = 1.9, 1H), 8.21 (s, 1H), 7.98 (d, J = 2.7, 1H), 7.93 (t, J = 6.1, 1H), 7.90 (s, 1H), 7.35 (d, J = 7.0, 1H), 7.30-7.25 (m, 1H), 7.02 (d, J = 8.2, 1H), 6.94 (t, J = 7.4, 1H), 4.45 (d, J = 6.0, 2H), 3.90 (s, 3H), 3.84 (s, 3H). | 1.974 min [402.1] m.p. 253-254° C. |

TABLE 1-continued

| No. | Structure and/or name | $^1$H NMR (400 MHz, DMSO-$d_6$); J [Hz]; δ [ppm] | LC-MS; rt; [M + H]$^+$ |
|---|---|---|---|
| 64 | Benzyl-{5-[5-(1-methyl-1H-pyrazol-4-yl)-1H-pyrrolo[2,3-b]pyridin-3-yl]-1,3,4-oxadiazol-2-yl}amine | 12.27 (s, 1H), 8.61 (d, J = 2.1, 1H), 8.40 (d, J = 2.0, 1H), 8.21 (s, 1H), 8.13 (t, J = 6.2, 1H), 7.99 (d, J = 2.8, 1H), 7.91 (d, J = 0.5, 1H), 7.43 (d, J = 7.5, 2H), 7.37 (dd, J = 10.4, 4.8, 2H), 7.28 (t, J = 7.3, 1H), 4.47 (d, J = 6.2, 2H), 3.90 (s, 3H). | 1.880 min [372.1] |
| 65 | 2-((2-Chlorophenyl)-{5-[5-(1-methyl-1H-pyrazol-4-yl)-1H-pyrrolo[2,3-b]-pyridin-3-yl]-1,3,4-oxadiazol-2-yl}-amino)-N,N-diethylacetamide | 12.35 (s, 1H), 8.58 (d, J = 2.1, 1H), 8.17 (d, J = 2.1, 1H), 8.12 (s, 1H), 7.95 (d, J = 2.6, 1H), 7.81 (d, J = 0.6, 1H), 7.78 (dd, J = 7.9, 1.7, 1H), 7.65 (dd, J = 7.9, 1.6, 1H), 7.50 (td, J = 7.7, 1.6, 1H), 7.44 (td, J = 7.7, 1.7, 1H), 4.74 (s, 2H), 3.90 (s, 3H), 3.37 (m, 2H), 3.31 (m, 2H), 1.18 (t, J = 7.1, 3H), 1.01 (t, J = 7.1, 3H). | 2.009 min [505.1] |
| 66 | 3-Chloro-N-cyclohexyl-4-{5-[5-(1-methyl-1H-pyrazol-4-yl)-1H-pyrrolo-[2,3-b]pyridin-3-yl]-1,3,4-oxadiazol-2-ylamino}benzamide | 12.43 (s, 1H), 9.95 (s, 1H), 8.63 (d, J = 2.1, 1H), 8.53 (d, J = 1.5, 1H), 8.48 (d, J = 2.0, 1H), 8.26 (d, J = 7.8, 1H), 8.22 (s, 1H), 8.08 (d, J = 2.5, 1H), 7.93 (s, 1H), 7.60 (q, J = 8.3, 2H), 3.90 (s, 3H), 3.80-3.70 (m, 1H), 1.80 (m, 2H), 1.73 (m, 2H), 1.61 (m, 1H), 1.37-1.24 (m, 4H), 1.19-1.06 (m, 1H). | 2.14 min [517.2] |
| 67 | 4-{5-[5-(1-Methyl-1H-pyrazol-4-yl)-1H-pyrrolo[2,3-b]pyridin-3-yl]-1,3,4-oxadiazol-2-ylamino}phenol | — | 1.667 min [374.1] |

TABLE 1-continued

| No. | Structure and/or name | ¹H NMR (400 MHz, DMSO-d₆); J [Hz]; δ [ppm] | LC-MS; rt; [M + H]⁺ |
|---|---|---|---|
| 68 | 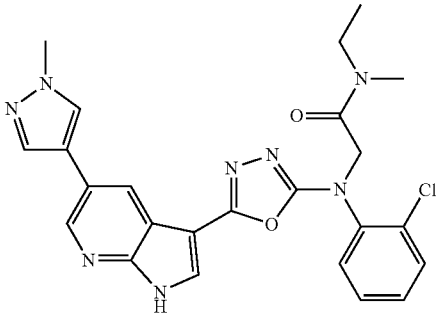 [SMILES: CCN(C)C(=O)CN(c1nnc(-c2c[nH]c3ncc(-c4cnn(C)c4)cc23)o1)c1ccccc1Cl]<br>2-((2-Chlorophenyl)-{5-[5-(1-methyl-1H-pyrazol-4-yl)-1H-pyrrolo[2,3-b]-pyridin-3-yl]-1,3,4-oxadiazol-2-yl}-amino)-N-ethyl-N-methylacetamide | 12.36 (s, 1H), 8.58 (d, J = 1.7, 1H), 8.16 (dd, J = 6.1, 2.0, 1H), 8.11 (s, 1H), 7.98 (dd, J = 16.7, 1.6, 1H), 7.80 (s, 1H), 7.78 (ddd, J = 7.8, 3.9, 1.6, 1H), 7.65 (d, J = 7.9, 1H), 7.49 (t, J = 7.1, 1H), 7.44 (t, J = 7.5, 1H), 4.82 (d, J = 7.8, 2H), 3.98 (s, 3H), 3.46-3.36 (m, 2H), 3.05 (s, 2H), 2.94-2.86 (m, 2H), 1.22 (t, J = 7.1, 2H), 1.10-1.03 (m, 2H). | 1.922 min [491.1] |
| 69 | 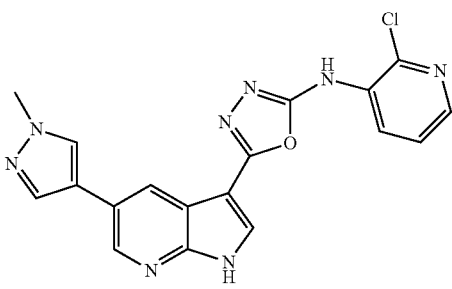 [SMILES: Cn1cc(-c2cnc3[nH]cc(-c4nnc(Nc5cccnc5Cl)o4)c3c2)cn1]<br>(2-Chloropyridin-3-yl)-{5-[5-(1-methyl-1H-pyrazol-4-yl)-1H-pyrrolo-[2,3-b]pyridin-3-yl]-1,3,4-oxadiazol-2-yl}amine | 12.46 (d, J = 1.9, 1H), 10.23-9.99 (m, 1H), 8.64 (d, J = 2.1, 1H), 8.59 (d, J = 7.5, 1H), 8.49 (d, J = 1.2, 1H), 8.24 (s, 1H), 8.14 (dd, J = 4.4, 1.2, 1H), 8.12 (d, J = 2.8, 1H), 7.94 (s, 1H), 7.52 (dd, J = 8.0, 4.6, 1H), 3.91 (s, 3H). | 1.791 min [393.0] |
| 70 | 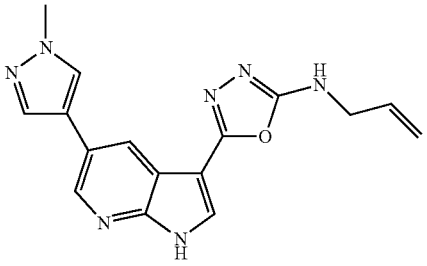 [SMILES: C=CCNc1nnc(-c2c[nH]c3ncc(-c4cnn(C)c4)cc23)o1]<br>Allyl-{5-[5-(1-methyl-1H-pyrazol-4-yl)-1H-pyrrolo[2,3-b]pyridin-3-yl]-1,3,4-oxadiazol-2-yl}amine | 12.30 (d, J = 1.8, 1H), 8.60 (d, J = 2.1, 1H), 8.41 (d, J = 2.1, 1H), 8.21 (s, 1H), 7.98 (d, J = 2.8, 1H), 7.92-7.90 (m, 1H), 7.75 (t, J = 5.9, 1H), 5.96 (ddt, J = 17.1, 10.5, 5.4, 1H), 5.29 (dq, J = 17.2, 1.6, 1H), 5.15 (dd, J = 10.3, 1.5, 1H), 3.90 (s, 3H). | 1.762 min [322.1] |

TABLE 1-continued

| No. | Structure and/or name | ¹H NMR (400 MHz, DMSO-d₆); J [Hz]; δ [ppm] | LC-MS; rt; [M + H]⁺ |
|---|---|---|---|
| 71 | ((2-Chlorophenyl)-{5-[5-(1-methyl-1H-pyrazol-4-yl)-1H-pyrrolo[2,3-b]-pyridin-3-yl]-1,3,4-oxadiazol-2-yl}-amino)acetic acid | 13.09 (br. s, 1H), 12.37 (s, 1H), 8.58 (d, J = 1.7, 1H), 8.17 (d, J = 1.7, 1H), 8.11 (s, 1H), 8.01 (d, J = 1.7, 1H), 7.81 (s, 1H), 7.74 (d, J = 7.7, 1H), 7.67 (d, J = 7.8, 1H), 7.51 (t, J = 7.1, 1H), 7.47 (dd, J = 10.9, 4.4, 1H), 4.55 (s, 2H), 3.90 (s, 3H). | 1.815 min [450.1] |
| 72 | {5-[5-(1-Methyl-1H-pyrazol-4-yl)-1H-pyrrolo[2,3-b]pyridin-3-yl]-1,3,4-oxadiazol-2-yl}pyridin-3-ylmethylamine | 12.31 (s, 1H), 8.64 (d, J = 1.9, 1H), 8.60 (d, J = 2.1, 1H), 8.49 (dd, J = 4.8, 1.6, 1H), 8.39 (d, J = 2.1, 1H), 8.20 (s, 1H), 8.18 (t, J = 6.1, 1H), 7.99 (d, J = 2.9, 1H), 7.90 (s, 1H), 7.83 (dt, J = 7.8, 1.9, 1H), 7.39 (dd, J = 7.8, 4.8, 1H), 4.49 (d, J = 6.1, 2H), 3.89 (s, 3H). | 1.363 min [373.1] |
| 73 | (2-Fluorobenzyl)-{5-[5-(1-methyl-1H-pyrazol-4-yl)-1H-pyrrolo[2,3-b]-pyridin-3-yl]-1,3,4-oxadiazol-2-yl}-amine | 12.31 (s, 1H), 8.64 (d, J = 1.9, 1H), 8.60 (d, J = 2.1, 1H), 8.49 (dd, J = 4.8, 1.6, 1H), 8.39 (d, J = 2.1, 1H), 8.20 (s, 1H), 8.18 (t, J = 6.1, 1H), 7.99 (d, J = 2.9, 1H), 7.90 (s, 1H), 7.83 (dt, J = 7.8, 1.9, 1H), 7.39 (dd, J = 7.8, 4.8, 1H), 4.49 (d, J = 6.1, 2H), 3.89 (s, 3H). | 1.899 min [390.1] |
| 74 | (3,5-Dimethylisoxazol-4-yl)-{5-[5-(1-methyl-1H-pyrazol-4-yl)-1H-pyrrolo-[2,3-b]pyridin-3-yl]-1,3,4-oxadiazol-2-yl}amine | 12.36 (d, J = 2.3, 1H), 9.40 (s, 1H), 8.61 (d, J = 2.1, 1H), 8.40 (d, J = 2.1, 1H), 8.21 (s, 1H), 8.02 (d, J = 2.8, 1H), 7.92-7.88 (m, 1H), 3.90 (s, 3H), 2.37 (s, 3H), 2.19 (s, 3H). | 1.660 min [377.1] |

TABLE 1-continued

| No. | Structure and/or name | ¹H NMR (400 MHz, DMSO-d₆); J [Hz]; δ [ppm] | LC-MS; rt; [M + H]⁺ |
|---|---|---|---|
| 75 | {5-[5-(1-Methyl-1H-pyrazol-4-yl)-1H-pyrrolo[2,3-b]pyridin-3-yl]-1,3,4-oxadiazol-2-yl}phenylamine | 12.41 (d, J = 2.1, 1H), 10.51 (s, 1H), 8.64 (d, J = 2.1, 1H), 8.49 (d, J = 2.1, 1H), 8.24 (s, 1H), 8.07 (d, J = 2.8, 1H), 7.94 (s, 1H), 7.64 (d, J = 7.8, 2H), 7.38 (t, J = 7.9, 2H), 7.02 (t, J = 7.3, 1H), 3.91 (s, 3H). | 1.984 min [358.1] m.p. 324-326° C. |
| 76 | Ethyl-{5-[5-(1-methyl-1H-pyrazol-4-yl)-1H-pyrrolo[2,3-b]pyridin-3-yl]-1,3,4-oxadiazol-2-yl}amine | 12.29 (d, J = 1.8, 1H), 8.60 (d, J = 2.1, 1H), 8.41 (d, J = 2.1, 1H), 8.22 (s, 1H), 7.96 (d, J = 2.8, 1H), 7.91 (d, J = 0.5, 1H), 7.51 (t, J = 5.6, 1H), 3.90 (s, 3H), 3.48 (q, J = 7.3, 2H), 1.21 (t, J = 7.2, 3H). | 1.606 min [310.1] |
| 77 | {5-[5-(1-Methyl-1H-pyrazol-4-yl)-1H-pyrrolo[2,3-b]pyridin-3-yl]-1,3,4-oxadiazol-2-yl}-(4-methylpyridin-3-yl)amine | 12.40 (s, 1H), 9.76 (s, 1H), 8.97 (s, 1H), 8.63 (d, J = 2.1, 1H), 8.45 (d, J = 2.1, 1H), 8.23 (d, J = 3.8, 2H), 8.06 (s, 1H), 7.93 (s, 1H), 7.29 (d, J = 4.8, 1H), 3.90 (s, 3H), 2.35 (s, 3H). | 1.436 min [373.1] |
| 78 | N-(3-Methyl-4-{5-[5-(1-methyl-1H-pyrazol-4-yl)-1H-pyrrolo[2,3-b]pyridin-3-yl]-1,3,4-oxadiazol-2-ylamino}phenyl)cyclohexane-carboxamide | 12.39 (d, J = 34.5, 1H), 9.70 (s, 1H), 9.36 (s, 1H), 8.62 (d, J = 2.1, 1H), 8.44 (d, J = 2.1, 1H), 8.20 (d, J = 9.6, 1H), 8.01 (d, J = 2.0, 1H), 7.91 (d, J = 0.6, 1H), 7.62 (d, J = 8.7, 1H), 7.51 (d, J = 2.1, 1H), 7.44 (dd, J = 8.7, 2.3, 1H), 3.90 (d, J = 3.5, 3H), 2.35-2.25 (m, 4H), 1.77 (m, 4H), 1.66 (m, 1H), 1.43 (m, 2H), 1.34-1.13 (m, 3H). | 2.066 min [497.2] |

TABLE 1-continued

| No. | Structure and/or name | $^1$H NMR (400 MHz, DMSO-$d_6$); J [Hz]; δ [ppm] | LC-MS; rt; [M + H]$^+$ |
|---|---|---|---|
| 79 | 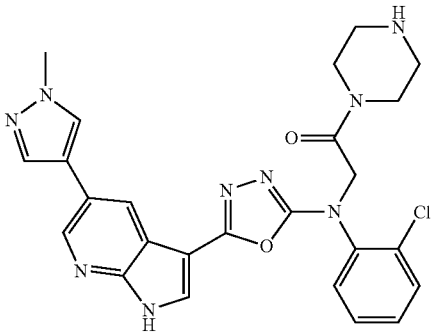 [SMILES: Cn1cc(-c2cnc3[nH]cc(-c4nnc(N(CC(=O)N5CCNCC5)c5ccccc5Cl)o4)c3c2)cn1]<br>2-((2-Chlorophenyl)-{5-[5-(1-methyl-1H-pyrazol-4-yl)-1H-pyrrolo[2,3-b]-pyridin-3-yl]-1,3,4-oxadiazol-2-yl}-amino)-1-piperazin-1-ylethanone | 12.40 (d, J = 2.4, 1H), 9.09 (s, 2H), 8.59 (d, J = 2.1, 1H), 8.12 (d, J = 2.1, 1H), 8.09 (s, 1H), 8.00 (d, J = 2.8, 1H), 7.79-7.77 (m, 2H), 7.68 (dd, J = 7.9, 1.6, 1H), 7.51 (td, J = 7.6, 1.7, 1H), 7.47 (td, J = 7.7, 1.8, 1H), 4.86 (s, 2H), 3.90 (d, J = 7.3, 3H), 3.72 (d, J = 17.5, 4H), 3.55 (d, J = 19.5, 9H), 3.17 (m, 2H), 3.09 (m, 2H). | 1.494 min [518.2] |
| 81 | 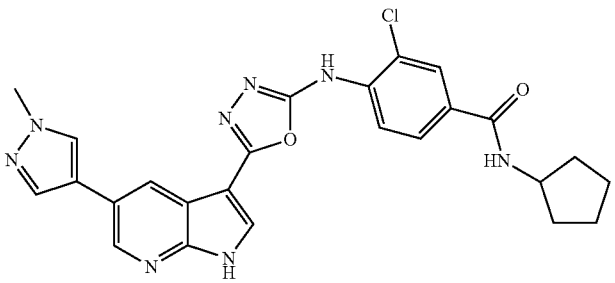 [SMILES: Cn1cc(-c2cnc3[nH]cc(-c4nnc(Nc5ccc(C(=O)NC6CCCC6)cc5Cl)o4)c3c2)cn1]<br>3-Chloro-N-cyclopentyl-4-{5-[5-(1-methyl-1H-pyrazol-4-yl)-1H-pyrrolo-[2,3-b]pyridin-3-yl]-1,3,4-oxadiazol-2-ylamino}benzamide | 12.44 (s, 1H), 9.95 (s, 1H), 8.63 (d, J = 2.1, 1H), 8.54 (s, 1H), 8.48 (d, J = 1.6, 1H), 8.34 (d, J = 7.2, 1H), 8.22 (s, 1H), 8.09 (d, J = 2.4, 1H), 7.93 (s, 1H), 7.63-7.56 (m, 2H), 4.27-4.18 (m, 1H), 3.91 (s, 3H), 2.88 (d, J = 11.1, 1H), 2.73 (s, 1H), 1.89 (m, 2H), 1.75-1.63 (m, 2H), 1.60-1.46 (m, 4H). | 2.047 min [503.1] |
| 82 | 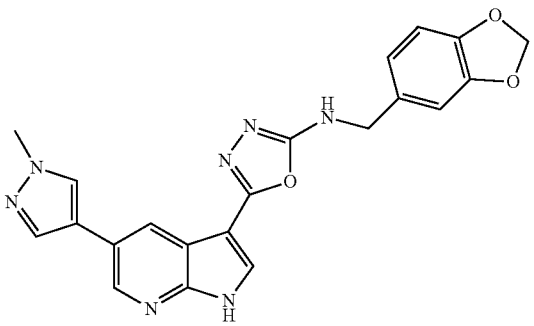 [SMILES: Cn1cc(-c2cnc3[nH]cc(-c4nnc(NCc5ccc6c(c5)OCO6)o4)c3c2)cn1]<br>Benzo-1,3-dioxol-5-ylmethyl-{5-[5-(1-methyl-1H-pyrazol-4-yl)-1H-pyrrolo[2,3-b]pyridin-3-yl]-1,3,4-oxadiazol-2-yl}amine | 12.35 (dd, J = 48.2, 2.4, 1H), 8.60 (d, J = 2.1, 1H), 8.40 (d, J = 2.1, 1H), 8.21 (s, 1H), 8.05 (t, J = 6.2, 1H), 7.99 (d, J = 2.8, 1H), 7.91 (s, 1H), 6.99 (d, J = 0.9, 1H), 6.93-6.85 (m, 2H), 5.99 (s, 2H), 4.36 (d, J = 6.1, 2H), 3.90 (s, 3H). | 1.918 min [416.1] m.p. 281-283° C. |

TABLE 1-continued

| No. | Structure and/or name | ¹H NMR (400 MHz, DMSO-d₆); J [Hz]; δ [ppm] | LC-MS; rt; [M + H]⁺ |
|---|---|---|---|
| 83 | (4-Methoxybenzyl)-{5-[5-(1-methyl-1H-pyrazol-4-yl)-1H-pyrrolo[2,3-b]-pyridin-3-yl]-1,3,4-oxadiazol-2-yl}-amine | 12.26 (s, 1H), 8.60 (d, J = 2.1, 1H), 8.39 (d, J = 2.0, 1H), 8.21 (s, 1H), 8.03 (t, J = 6.1, 1H), 7.98 (d, J = 2.8, 1H), 7.90 (d, J = 0.6, 1H), 7.34 (d, J = 8.7, 2H), 6.93-6.89 (m, 2H), 4.38 (d, J = 6.1, 2H), 3.89 (s, 3H), 3.73 (s, 3H). | 1.888 min [402.1] |
| 84 | (3-Methoxyphenyl)-{5-[5-(1-methyl-1H-pyrazol-4-yl)-1H-pyrrolo[2,3-b]-pyridin-3-yl]-1,3,4-oxadiazol-2-yl}-amine | 12.38 (s, 1H), 10.66-10.42 (m, 1H), 8.63 (d, J = 2.1, 1H), 8.47 (t, J = 7.0, 1H), 8.25 (s, 1H), 8.06 (d, J = 2.8, 1H), 7.94 (s, 1H), 7.36 (t, J = 2.2, 1H), 7.26 (t, J = 8.1, 1H), 7.15 (dd, J = 8.0, 1.4, 1H), 6.60 (dd, J = 8.1, 2.1, 1H), 3.91 (s, 3H), 3.78 (s, 3H). | 2.015 min [388.1] |
| 85 | [{5-[5-(1-Methyl-1H-pyrazol-4-yl)-1H-pyrrolo[2,3-b]pyridin-3-yl]-1,3,4-oxadiazol-2-yl}-(2-methylpyridin-3-yl)amino]acetonitrile | 12.44 (d, J = 2.2, 1H), 8.64 (dd, J = 4.9, 1.4, 1H), 8.60 (d, J = 2.1, 1H), 8.21 (d, J = 2.1, 1H), 8.15 (s, 1H), 8.07 (dd, J = 7.4, 1.9, 2H), 7.84 (d, J = 0.7, 1H), 7.54 (dd, J = 8.0, 4.9, 1H), 5.08 (s, 2H), 3.91 (s, 3H), 2.53 (s, 3H). | 1.569 min [412.1] |
| 86 | ((2-Fluorophenyl)-{5-[5-(1-methyl-1H-pyrazol-4-yl)-1H-pyrrolo[2,3-b]-pyridin-3-yl]-1,3,4-oxadiazol-2-yl}-amino)acetonitrile | 12.42 (t, J = 14.5, 1H), 8.60 (d, J = 2.1, 1H), 8.21 (d, J = 2.1, 1H), 8.12 (s, 1H), 8.06 (d, J = 2.8, 1H), 7.82 (d, J = 0.5, 1H), 7.73 (td, J = 8.0, 1.6, 1H), 7.58-7.47 (m, 2H), 7.41 (td, J = 7.7, 1.4, 1H), 5.09 (s, 2H), 3.90 (s, 3H). | 1.869 min [415.1] |

TABLE 1-continued

| No. | Structure and/or name | ¹H NMR (400 MHz, DMSO-d$_6$); J [Hz]; δ [ppm] | LC-MS; rt; [M + H]⁺ |
|---|---|---|---|
| 87 | 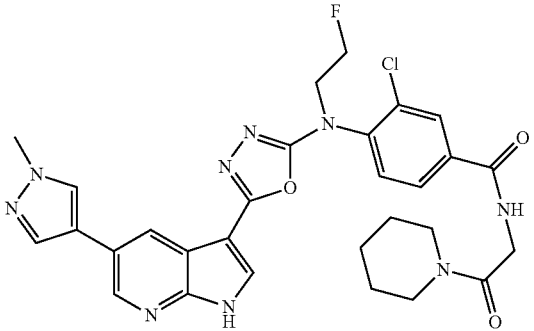 [SMILES: Cn1cc(-c2cnc3[nH]cc(-c4nnc(N(CCF)c5ccc(C(=O)NCC(=O)N6CCCCC6)cc5Cl)o4)c3c2)cn1]<br>3-Chloro-4-((2-fluoroethyl)-{5-[5-(1-methyl-1H-pyrazol-4-yl)-1H-pyrrolo-[2,3-b]pyridin-3-yl]-1,3,4-oxadiazol-2-ylamino}-N-(2-oxo-2-piperidin-1-ylethyl)benzamide | 12.37 (s, 1H), 8.77 (t, J = 5.7, 1H), 8.58 (d, J = 2.1, 1H), 8.17 (d, J = 2.0, 1H), 8.16 (d, J = 2.1, 1H), 8.06 (s, 1H), 8.01 (s, 1H), 7.96 (dd, J = 8.4, 2.1, 1H), 7.81 (d, J = 8.9, 2H), 4.82 (t, J = 4.7, 1H), 4.72 (t, J = 4.7, 1H), 4.27 (t, J = 4.6, 1H), 4.21 (t, J = 4.6, 1H), 4.13 (t, J = 6.9, 2H), 3.90 (s, 3H), 1.64-1.38 (m, 6H). | 1.942 min [606.2] |
| 87a | 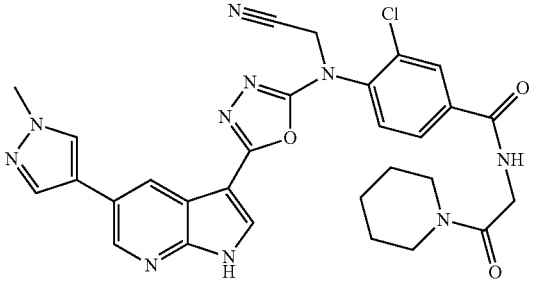 [SMILES: Cn1cc(-c2cnc3[nH]cc(-c4nnc(N(CC#N)c5ccc(C(=O)NCC(=O)N6CCCCC6)cc5Cl)o4)c3c2)cn1]<br>3-Chloro-4-(cyanomethyl-{5-[5-(1-methyl-1H-pyrazol-4-yl)-1H-pyrrolo-[2,3-b]pyridin-3-yl]-1,3,4-oxadiazol-2-yl}amino)-N-(2-oxo-2-piperidin-1-ylethyl)benzamide | 12.43 (s, 1H), 8.78 (t, J = 5.7, 1H), 8.60 (d, J = 2.1, 1H), 8.23 (d, J = 2.0, 1H), 8.22 (d, J = 2.1, 1H), 8.09 (s, 1H), 8.06 (s, 1H), 8.02 (dd, J = 8.4, 2.1, 1H), 7.86 (d, J = 8.4, 1H), 7.84 (d, J = 0.5, 1H), 5.12 (s, 2H), 4.13 (d, J = 5.7, 2H), 3.90 (s, 3H), 1.64-1.37 (m, 6H). | 1.900 min [599.2] |

Comparative compounds from WO 2010/020308

| No. | Structure/name | Number in WO 2010/020308 |
|---|---|---|
| 88 | 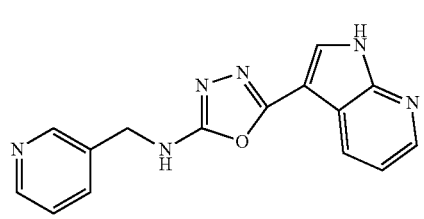 [SMILES: c1cncc(CNc2nnc(-c3c[nH]c4ncccc34)o2)c1]<br>Pyridin-3-ylmethyl-[5-(1H-pyrrolo-[2,3-b]pyridin-3-yl)-1,3,4-oxadiazol-2-yl]amine | A8 |

| No. | Structure/name | Number in WO 2010/020308 |
|---|---|---|
| 89 | (3,5-Dimethoxyphenyl)-[5-(1H-pyrrolo[2,3-b]pyridin-3-yl)-1,3,4-oxadiazol-2-yl]amine | A7 |
| 90 | (3-Methoxybenzyl)-{5-[5-(1H-pyrazol-4-yl)-1H-pyrrolo[2,3-b]pyridin-3-yl]-1,3,4-oxadiazol-2-yl}amine | A6 |
| 95 | (3-Methoxybenzyl)-[5-(1H-pyrrolo-[2,3-b]pyridin-3-yl)-1,3,4-oxadiazol-2-yl]amine | A10 |

TABLE I

Inhibition of PDK1
$IC_{50}$ of compounds according to the invention and comparative compounds from WO 2010/020308

| Compound No. | $IC_{50}$ [PDK1] enzymatic [M] | $IC_{50}$ [PDK1] cellular [M] |
|---|---|---|
| 1 | 1.79 | >10 |
| 2 | 2.20 | |
| 3 | | 0.028 |
| 21 | 0.65 | >10 |
| 22 | 5.3 | |
| 23 | 0.61 | |
| 24 | 0.8 | |
| 25 | 0.77 | >10 |
| 26 | 0.55 | |
| 27 | 6.1 | |
| 28 | 0.68 | |
| 29 | 0.36 | |
| 30 | 0.88 | |
| 31 | 0.3 | |
| 32 | 0.74 | |
| 33 | 0.035 | >10 |
| 34 | 0.045 | |
| 35 | 0.27 | 0.45 |
| 36 | 0.066 | |
| 37 | 0.045 | |
| 38 | 0.15 | |
| 39 | 0.063 | |
| 40 | 0.024 | |
| 41 | 0.039 | |
| 42 | 0.053 | |
| 43 | 0.083 | |
| 44 | 0.21 | |
| 45 | 0.023 | 0.003 |
| 46 | 0.038 | 0.028 |
| 48 | 0.041 | 0.99 |
| 49 | 0.046 | 0.031 |
| 50 | 0.058 | 0.051 |
| 51 | 0.062 | 3.2 |
| 52 | 0.068 | 0.26 |
| 53 | 0.08 | 0.76 |
| 54 | 0.089 | 0.31 |
| 55 | 0.092 | 3.2 |
| 56 | 0.11 | 2.5 |
| 57 | 0.11 | 3.2 |
| 58 | 0.12 | 2.1 |

TABLE I-continued

Inhibition of PDK1
IC$_{50}$ of compounds according to the invention and
comparative compounds from WO 2010/020308

| Compound No. | IC$_{50}$ [PDK1] enzymatic [M] | IC$_{50}$ [PDK1] cellular [M] |
| --- | --- | --- |
| 59 | 0.14 | 2.4 |
| 60 | 0.14 | 3.3 |
| 61 | 0.15 | 1.1 |
| 62 | 0.16 | 1.2 |
| 63 | 0.16 | 3.0 |
| 64 | 0.17 | 0.003 |
| 65 | 0.18 | 1.7 |
| 66 | 0.18 | >10 |
| 67 | 0.19 | >10 |
| 68 | 0.19 | 2.6 |
| 69 | 0.2 | >10 |
| 70 | 0.21 | |
| 71 | 0.22 | >10 |
| 72 | 0.23 | 3.7 |
| 73 | 0.24 | 3.2 |
| 74 | 0.3 | 14 |
| 75 | 0.3 | >10 |
| 76 | 0.33 | 0.037 |
| 77 | 0.34 | >10 |
| 78 | 0.36 | >10 |
| 79 | 0.51 | 10 |
| 80 | 0.58 | >10 |
| 81 | 0.71 | >10 |
| 82 | 0.79 | 1.3 |
| 83 | 0.9 | |
| 84 | 1.3 | |
| 85 | 0.6 | |
| 86 | 0.054 | |
| 87 | 0.067 | |
| 87a | 0.170 | |
| 88 | >10 | |
| 89 | >10 | |
| 90 | >10 | |
| 95 | >10 | |

In the case of inhibition of PDK1 (enzymatic), the compounds from the prior art (No. 88, 89, 90, 95) have lower activity than the compounds according to the invention.

The following examples relate to medicaments:

EXAMPLE A

Injection Vials

A solution of 100 g of an active compound of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active compound.

EXAMPLE B

Suppositories

A mixture of 20 g of an active compound of the formula I with 100 g of soya lecithin and 1400 g of cocoa butter is melted, poured into moulds and allowed to cool. Each suppository contains 20 mg of active compound.

EXAMPLE C

Solution

A solution is prepared from 1 g of an active compound of the formula I, 9.38 g of NaH$_2$PO$_4$.2H$_2$O, 28.48 g of Na$_2$HPO$_4$.12H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active compound of the formula I are mixed with 99.5 g of Vaseline under aseptic conditions.

EXAMPLE E

Tablets

A mixture of 1 kg of active compound of the formula I, 4 kg of lactose, 1.2 kg of potato starch, 0.2 kg of talc and 0.1 kg of magnesium stearate is pressed in a conventional manner to give tablets in such a way that each tablet contains 10 mg of active compound.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active compound of the formula I are introduced into hard gelatine capsules in a conventional manner in such a way that each capsule contains 20 mg of the active compound.

EXAMPLE H

Ampoules

A solution of 1 kg of active compound of the formula I in 60 l of bidistilled water is sterile filtered, transferred into ampoules, lyophilised under sterile conditions and sealed under sterile conditions. Each ampoule contains 10 mg of active compound.

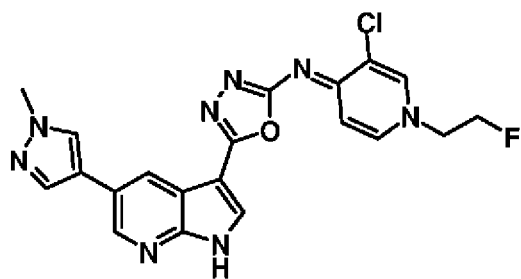

The invention claimed is:
1. a compound of the formula I

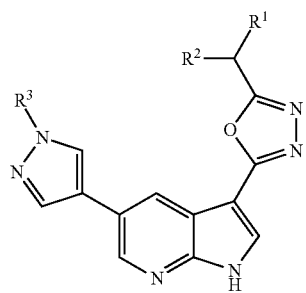

in which
R¹ denotes H, A, CH₂CN, CH₂CONH₂, CH₂CONHA', CH₂CONA'₂, CH₂COOH, CH₂COOA' or CH₂COHet¹,
R² denotes (CH₂)$_n$Ar, COAr, (CH₂)$_n$Het, Cyc, Alk or A,
R³ denotes CH₃ or (CH₂)$_n$NHCOOA',
R⁴ denotes phenyl,
Alk denotes unbranched or branched alkenyl having 2-6 C atoms,
A denotes unbranched or branched alkyl having 1-8 C atoms, in which one or two non-adjacent CH₂ and/or CH groups may be replaced by O, N and/or S atoms and/or 1-7 H atoms may be replaced by F and/or Cl,
A' denotes unbranched or branched alkyl having 1-4 C atoms,
Cyc denotes cycloalkyl having 3-7 C atoms,
Ar denotes phenyl which is unsubstituted or mono-, di- or trisubstituted by Hal, A, (CH₂)₂CN, (CH₂)₂COOH, (CH₂)₂COOA, (CH₂)₂OH, (CH₂)₂OA, COHet¹, O(CH₂)₂R⁴, NO₂, CONHHet¹, NHCOCyc, CONH(CH₂)₂CONH₂, CONH(CH₂)₂CONHA', CONH(CH₂)₂CONA'₂, CONH₂, CONHA', CONA'₂, NHCOAlk, CONHCH(R⁴)CONH₂, CONH(CH₂)$_n$CONHHet¹, CONH(CH₂)$_n$COHet¹ and/or CONH(CH₂)$_n$Cyc,
Het denotes a mono- or bicyclic aromatic heterocycle having 1 to 4 N, and/or O and/or S atoms which is unsubstituted or mono- or disubstituted by Hal and/or A,
Het¹ denotes a monocyclic saturated, unsaturated or aromatic heterocycle having 1 to 4 N, and/or O and/or S atoms which is unsubstituted or mono- or disubstituted by A,
Hal denotes F, Cl, Br or I,
n denotes 0, 1 or 2,
or pharmaceutically acceptable salts, tautomers and stereoisomers thereof.

2. Compounds according to claim 1 in which
Het denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzodioxolyl, benzotriazolyl, quinolinyl, quinoxalinyl, quinazolinyl, pyrrolopyridinyl, purinyl, indolyl or indazolyl, each of which is unsubstituted or mono- or disubstituted by Hal and/or A,
or pharmaceutically acceptable salts, tautomers and stereoisomers thereof.

3. Compounds according to claim 1 in which
Het¹ denotes piperidinyl, pyrrolidinyl, morpholinyl, piperazinyl, imidazolidinyl, oxazolidinyl, tetrahydropyranyl, dihydroisoindolyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl or pyrazinyl, each of which is unsubstituted or mono- or disubstituted by A,
or pharmaceutically acceptable salts, tautomers and stereoisomers thereof.

4. Compounds according to claim 1 in which
R¹ denotes H, A, CH₂CN, CH₂CONH₂, CH₂CONHA', CH₂CONA'₂, CH₂COOH, CH₂COOA' or CH₂COHet¹,
R² denotes (CH₂)$_n$Ar, COAr, (CH₂)$_n$Het, Cyc, Alk or A,
R³ denotes CH₃ or (CH₂)$_n$NHCOOA',
R⁴ denotes phenyl,
Alk denotes unbranched or branched alkenyl having 2-6 C atoms,
A denotes unbranched or branched alkyl having 1-8 C atoms, in which one or two non-adjacent CH₂ and/or CH groups may be replaced by O, N and/or S atoms and/or 1-7 H atoms may be replaced by F and/or Cl,
A' denotes unbranched or branched alkyl having 1-4 C atoms,
Cyc denotes cycloalkyl having 3-7 C atoms,
Ar denotes phenyl which is unsubstituted or mono-, di- or trisubstituted by Hal, A, (CH₂)₂CN, (CH₂)₂COOH, (CH₂)₂COOA, (CH₂)₂OH, (CH₂)₂OA, COHet¹, O(CH₂)₂R⁴, NO₂, CONHHet¹, NHCOCyc, CONH(CH₂)₂CONH₂, CONH(CH₂)₂CONHA', CONH(CH₂)₂CONA'₂, CONH₂, CONHA', CONA'₂, NHCOAlk, CONHCH(R⁴)CONH₂, CONH(CH₂)$_n$CONHHet¹, CONH(CH₂)$_n$COHet¹ and/or CONH(CH₂)$_n$Cyc,
Het denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzodioxolyl, benzotriazolyl, quinolinyl, quinoxalinyl, quinazolinyl, pyrrolopyridinyl, purinyl, indolyl or indazolyl, each of which is unsubstituted or mono- or disubstituted by Hal and/or A,
Het¹ denotes piperidinyl, pyrrolidinyl, morpholinyl, piperazinyl, imidazolidinyl, oxazolidinyl, tetrahydropyranyl, dihydroisoindolyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl or pyrazinyl, each of which is unsubstituted or mono- or disubstituted by A,
Hal denotes F, Cl, Br or I,
n denotes 0, 1 or 2,
or pharmaceutically acceptable salts, tautomers and stereoisomers thereof.

5. A compound, which is one of the following compounds

| Compound No. | Name and/or structure |
|---|---|
| 1 | 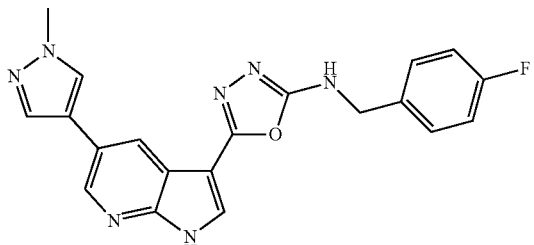<br>(4-Fluorobenzyl)-{5-[5-(1-methyl-1H-pyrazol-4-yl)-1H-pyrrolo-[2,3-b]pyridin-3-yl]-1,3,4-oxadiazol-2-yl}amine |

-continued

| Compound No. | Name and/or structure |
|---|---|
| 2 | 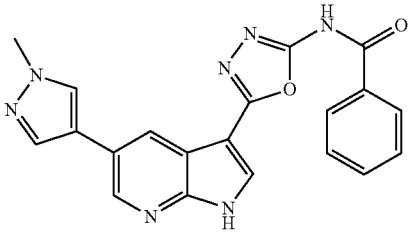 [SMILES: Cn1cc(-c2cnc3[nH]cc(-c4nnc(NC(=O)c5ccccc5)o4)c3c2)cn1]
N-{5-[5-(1-Methyl-1H-pyrazol-4-yl)-1H-pyrrolo[2,3-b]pyridin-3-yl]-1,3,4-oxadiazol-2-yl}benzamide |
| 3 | 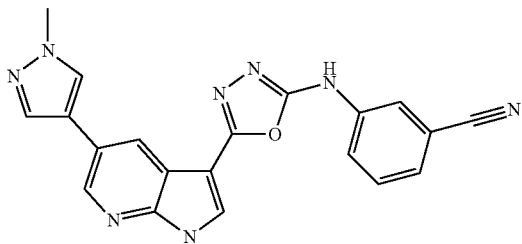
3-{5-[5-(1-Methyl-1H-pyrazol-4-yl)-1H-pyrrolo[2,3-b]pyridin-3-yl]-1,3,4-oxadiazol-2-ylamino}benzonitrile |
| 21 | 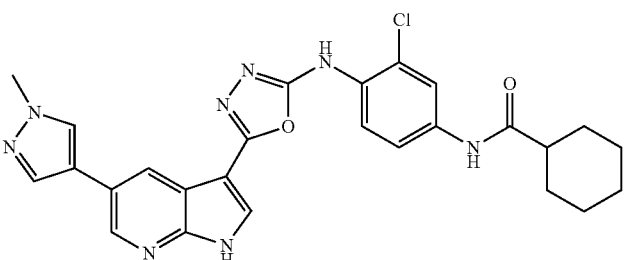
N-(3-Chloro-4-{5-[5-(1-methyl-1H-pyrazol-4-yl)-1H-pyrrolo[2,3-b]-pyridin-3-yl]-1,3,4-oxadiazol-2-ylamino}phenyl)cyclohexane-carboxamide |
| 22 | 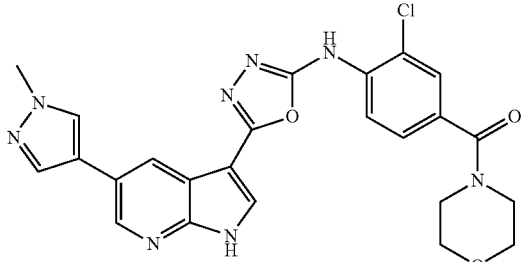
(3-Chloro-4-{5-[5-(1-methyl-1H-pyrazol-4-yl)-1H-pyrrolo[2,3-b]-pyridin-3-yl]-1,3,4-oxadiazol-2-ylamino}phenyl)morpholin-4-ylmethanone |
| 24 | 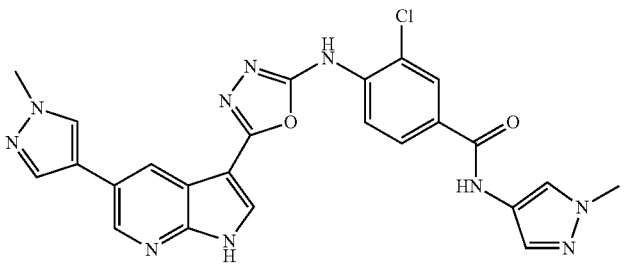 [SMILES: Cn1cc(NC(=O)c2ccc(Nc3nnc(-c4c[nH]c5ncc(-c6cnn(C)c6)cc45)o3)c(Cl)c2)cn1]
3-Chloro-N-(1-methyl-1H-pyrazol-4-yl)-4-{5-[5-(1-methyl-1H-pyrazol-4-yl)-1H-pyrrolo[2,3-b]pyridin-3-yl]-1,3,4-oxadiazol-2-ylamino}benzamide |

| Compound No. | Name and/or structure |
|---|---|
| 25 | 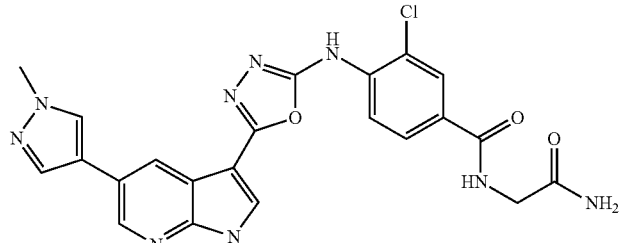<br>N-Carbamoylmethyl-3-chloro-4-{5-[5-(1-methyl-1H-pyrazol-4-yl)-1H-pyrrolo[2,3-b]pyridin-3-yl]-1,3,4-oxadiazol-2-ylamino}benzamide |
| 26 | 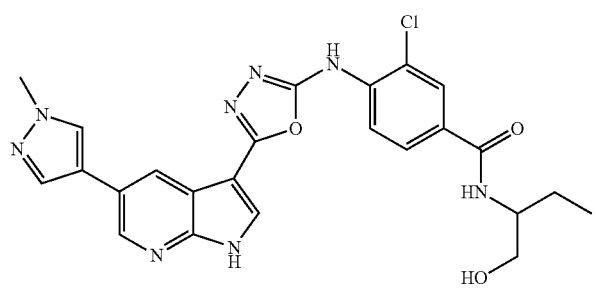 [SMILES: CCC(CO)NC(=O)c1ccc(Nc2nnc(-c3c[nH]c4ncc(-c5cnn(C)c5)cc34)o2)c(Cl)c1]<br>3-Chloro-N-(1-hydroxymethylpropyl)-4-{5-[5-(1-methyl-1H-pyrazol-4-yl)-1H-pyrrolo[2,3-b]pyridin-3-yl]-1,3,4-oxadiazol-2-ylamino}-benzamide |
| 27 | 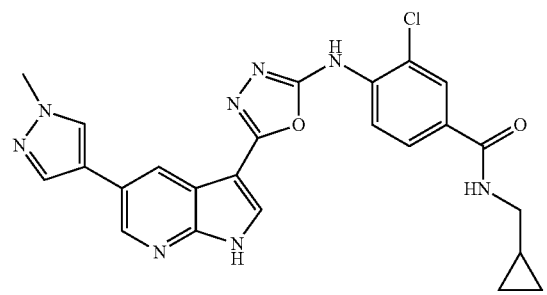 [SMILES: Cn1cc(-c2cnc3[nH]cc(-c4nnc(Nc5ccc(C(=O)NCC6CC6)cc5Cl)o4)c3c2)cn1]<br>3-Chloro-N-cyclopropylmethyl-4-{5-[5-(1-methyl-1H-pyrazol-4-yl)-1H-pyrrolo[2,3-b]pyridin-3-yl]-1,3,4-oxadiazol-2-ylamino}benzamide |
| 28 | 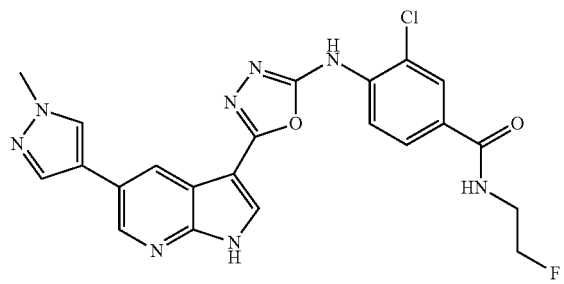 [SMILES: Cn1cc(-c2cnc3[nH]cc(-c4nnc(Nc5ccc(C(=O)NCCF)cc5Cl)o4)c3c2)cn1]<br>3-Chloro-N-(2-fluoroethyl)-4-{5-[5-(1-methyl-1H-pyrazol-4-yl)-1H-pyrrolo[2,3-b]pyridin-3-yl]-1,3,4-oxadiazol-2-ylamino}benzamide |

| Compound No. | Name and/or structure |
|---|---|
| 29 | 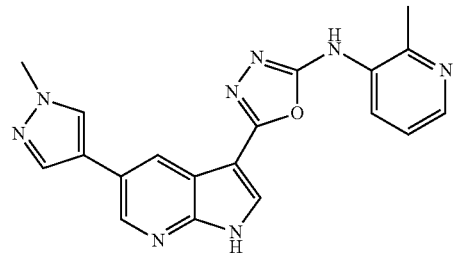 [SMILES: Cc1ncccc1Nc1nnc(-c2c[nH]c3ncc(-c4cnn(C)c4)cc23)o1]<br>{5-[5-(1-Methyl-1H-pyrazol-4-yl)-1H-pyrrolo[2,3-b]pyridin-3-yl]-1,3,4-oxadiazol-2-yl-(2-methylpyridin-3-yl)amine |
| 30 | 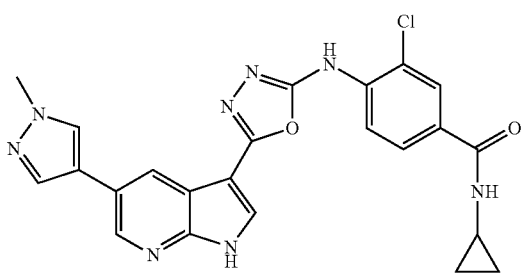 [SMILES: Cn1cc(-c2cnc3[nH]cc(-c4nnc(Nc5ccc(C(=O)NC6CC6)cc5Cl)o4)c3c2)cn1]<br>3-Chloro-N-cyclopropyl-4-{5-[5-(1-methyl-1H-pyrazol-4-yl)-1H-pyrrolo[2,3-b]pyridin-3-yl]-1,3,4-oxadiazol-2-ylamino)benzamide |
| 31 | 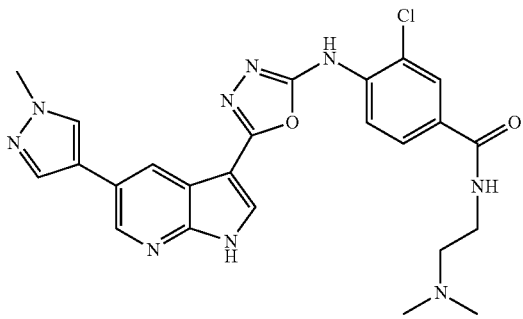 [SMILES: CN(C)CCNC(=O)c1ccc(Nc2nnc(-c3c[nH]c4ncc(-c5cnn(C)c5)cc34)o2)c(Cl)c1]<br>3-Chloro-N-(2-dimethylaminoethyl)-4-{5 [5-(1-methyl-1H-pyrazol-4-yl)-1H-pyrrolo[2,3-b]pyridin-3-yl]-1,3,4-oxadiazol-2-ylamino}-benzamide |
| 32 | 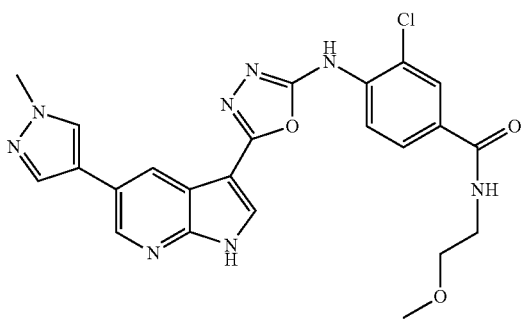 [SMILES: COCCNC(=O)c1ccc(Nc2nnc(-c3c[nH]c4ncc(-c5cnn(C)c5)cc34)o2)c(Cl)c1]<br>3-Chloro-N-(2-methoxyethyl)-4-(5-[5-(1-methyl-1H-pyrazol-4-yl)-1H-pyrrolo[2,3-b]pyridin-3-yl]-1,3,4-oxadiazol-2-ylamino}benzamide |

| Compound No. | Name and/or structure |
|---|---|
| 33 | 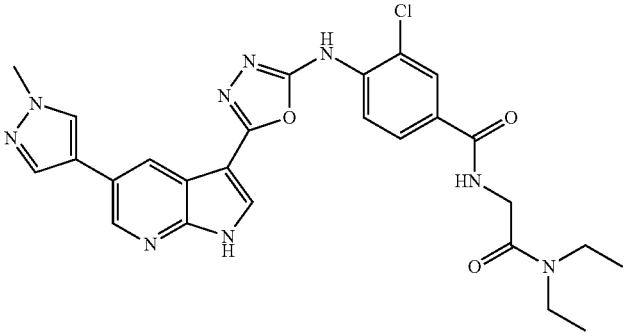 [SMILES: CCN(CC)C(=O)CNC(=O)c1ccc(Nc2nnc(-c3c[nH]c4ncc(-c5cnn(C)c5)cc34)o2)c(Cl)c1]<br>3-Chloro-N-diethylcarbamoylmethyl-4-{5-[5-(1-methyl-1H-pyrazol-4-yl)-1H-pyrrolo[2,3-b]pyridin-3-yl]-1,3,4-oxadiazol-2-ylamino}-benzamide |
| 34 | 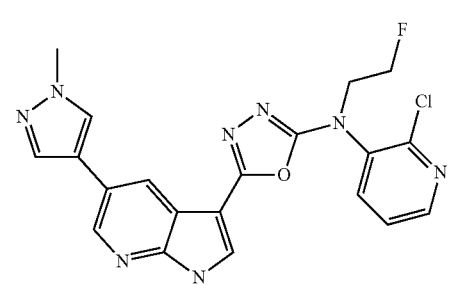<br>(2-Chloropyridin-3-yl)-(2-fluoroethyl)-{5-[5-(1-methyl-1H-pyrazol-4-yl)-1H-pyrrolo[2,3-b]pyridin-3-yl]-1,3,4-oxadiazol-2-yl}amine |
| 35 | 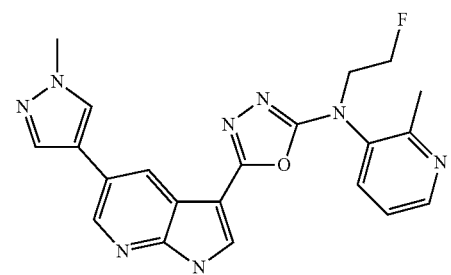<br>(2-Fluoroethyl)-{5-[5-(1-methyl-1H-pyrazol-4-yl)-1H-pyrrolo[2,3-b]-pyridin-3-yl]-1,3,4-oxadiazol-2-yl}-(2-methylpyridin-3-yl)amine |
| 36 | 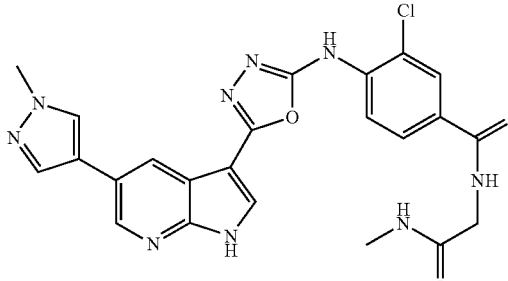<br>3-Chloro-N-methylcarbamoylmethyl-4-{5-[5-(1-methyl-1H-pyrazol-4-yl)-1H-pyrrolo[2,3-b]pyridin-3-yl]-1,3,4-oxadiazol-2-ylamino}-benzamide |

| Compound No. | Name and/or structure |
|---|---|
| 37 | 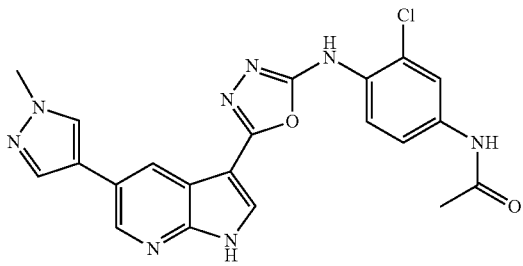 [SMILES: CC(=O)Nc1ccc(Nc2nnc(-c3c[nH]c4ncc(-c5cnn(C)c5)cc34)o2)c(Cl)c1]<br>N-(3-Chloro-4-{5-[5-(1-methyl-1H-pyrazol-4-yl)-1H-pyrrolo[2,3-b]-pyridin-3-yl]-1,3,4-oxadiazol-2-ylamino}phenyl)acetamide |
| 38 | 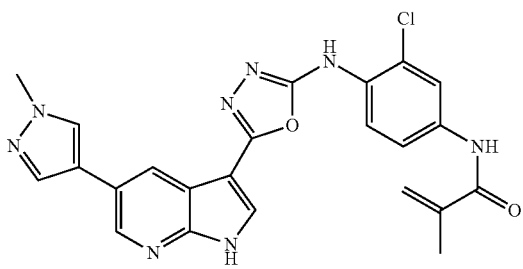 [SMILES: C=C(C)C(=O)Nc1ccc(Nc2nnc(-c3c[nH]c4ncc(-c5cnn(C)c5)cc34)o2)c(Cl)c1]<br>N-(3-Chloro-4-{5-[5-(1-methyl-1H-pyrazol-4-yl)-1H-pyrrolo[2,3-b]-pyridin-3-yl]-1,3,4-oxadiazol-2-ylamino}phenyl)-2-methylacrylamide |
| 39 | 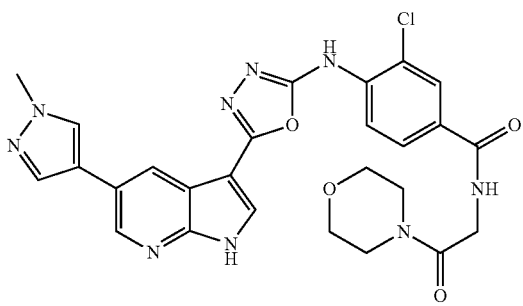 [SMILES: Cn1cc(-c2cnc3[nH]cc(-c4nnc(Nc5ccc(C(=O)NCC(=O)N6CCOCC6)cc5Cl)o4)c3c2)cn1]<br>3-Chloro-4-{5-[5-(1-methyl-1H-pyrazol-4-yl)-1H-pyrrolo[2,3-b]-pyridin-3-yl]-1,3,4-oxadiazol-2-ylamino}-N-(2-morpholin-4-yl-2-oxoethyl)benzamide |
| 40 | 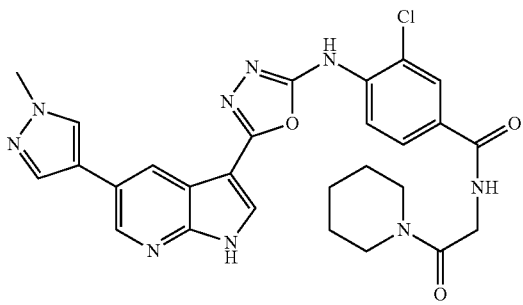 [SMILES: Cn1cc(-c2cnc3[nH]cc(-c4nnc(Nc5ccc(C(=O)NCC(=O)N6CCCCC6)cc5Cl)o4)c3c2)cn1]<br>3-Chloro-4-{5-[5-(1-methyl-1H-pyrazol-4-yl)-1H-pyrrolo[2,3-b]-pyridin-3-yl]-1,3,4-oxadiazol-2-ylamino}-N-(2-oxo-2-piperidin-1-ylethyl)benzamide |

| Compound No. | Name and/or structure |
|---|---|
| 41 | 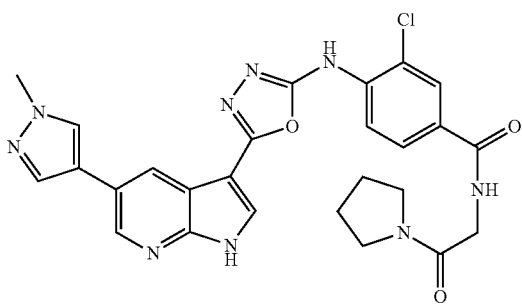 [SMILES: Cn1cc(-c2cnc3[nH]cc(-c4nnc(Nc5ccc(C(=O)NCC(=O)N6CCCC6)cc5Cl)o4)c3c2)cn1]<br>3-Chloro-4-{5-[5-(1-methyl-1H-pyrazol-4-yl)-1H-pyrrolo[2,3-b]-pyridin-3-yl]-1,3,4-oxadiazol-2-ylamino}-N-(2-oxo-2-pyrrolidin-1-ylethyl)benzamide |
| 42 | 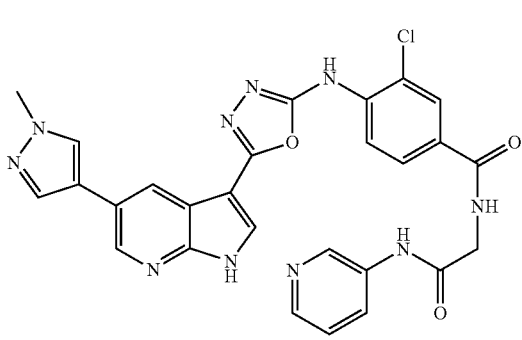 [SMILES: Cn1cc(-c2cnc3[nH]cc(-c4nnc(Nc5ccc(C(=O)NCC(=O)Nc6cccnc6)cc5Cl)o4)c3c2)cn1]<br>3-Chloro-4-{5-[5-(1-methyl-1H-pyrazol-4-yl)-1H-pyrrolo[2,3-b]-pyridin-3-yl]-1,3,4-oxadiazol-2-ylamino}-N-(pyridin-3-yl-carbamoylmethyl)benzamide |
| 43 | 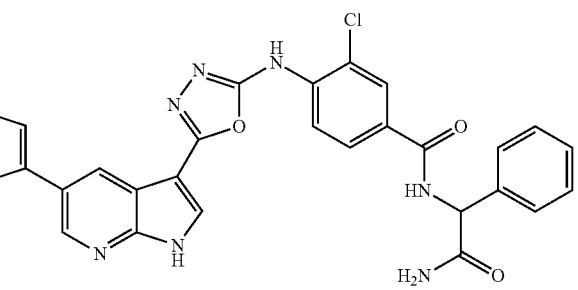<br>N-(Carbamoylphenylmethyl)-3-chloro-4-{5-[5-(1-methyl-1H-pyrazol-4-yl)-1H-pyrrolo [2,3-b]pyridin-3-yl]-1,3,4-oxadiazol-2-ylamino}-benzamide |
| 44 | 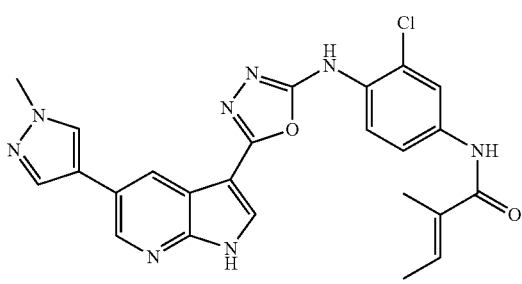 [SMILES: C/C=C(\C)C(=O)Nc1ccc(Nc2nnc(-c3c[nH]c4ncc(-c5cnn(C)c5)cc34)o2)c(Cl)c1]<br>N-(3-Chloro-4-{5-[5-(1-methyl-1H-pyrazol-4-yl)-1H-pyrrolo[2,3-b]-pyridin-3-yl}-1,3,4-oxadiazol-2-ylamino}phenyl)-(E)-2-methylbut-2-enamide |

-continued

| Compound No. | Name and/or structure |
|---|---|
| 45 | 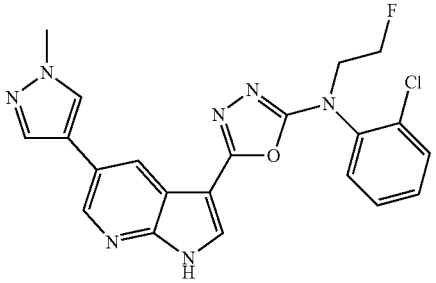 [SMILES: Cn1cc(-c2cnc3[nH]cc(-c4nnc(N(CCF)c5ccccc5Cl)o4)c3c2)cn1]<br>(2-Chlorophenyl)-(2-fluoroethyl)-{5-[5-(1-methyl-1H-pyrazol-4-yl)-1H-pyrrolo[2,3-b]pyridin-3-yl]-1,3,4-oxadiazol-2-yl}amine |
| 46 | 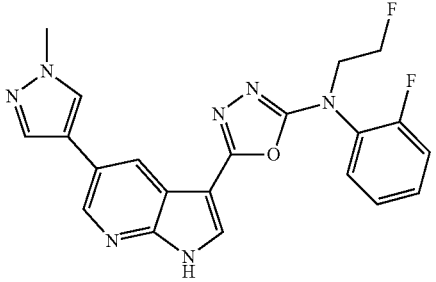 [SMILES: Cn1cc(-c2cnc3[nH]cc(-c4nnc(N(CCF)c5ccccc5F)o4)c3c2)cn1]<br>(2-Fluoroethyl)-(2-fluorophenyl)-{5-[5-(1-methyl-1H-pyrazol-4-yl)-1H-pyrrolo[2,3-b]pyridin-3-yl]-1,3,4-oxadiazol-2-yl}amine |
| 48 | 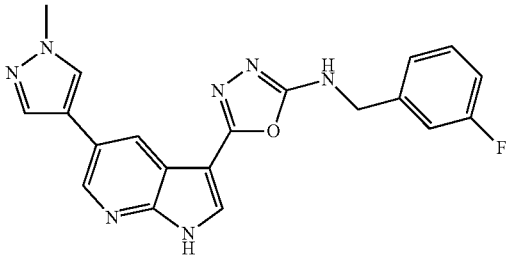 [SMILES: Cn1cc(-c2cnc3[nH]cc(-c4nnc(NCc5cccc(F)c5)o4)c3c2)cn1]<br>(3-Fluorobenzyl)-{5-[5-(1-methyl-1H-pyrazol-4-yl)-1H-pyrrolo-[2,3-b]pyridin-3-yl]-1,3,4-oxadiazol-2-yl}amine |
| 49 | 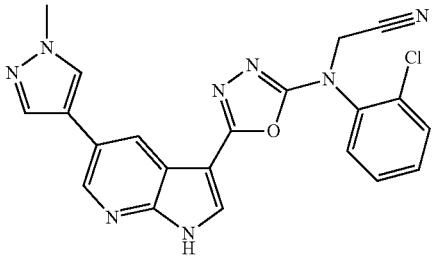 [SMILES: Cn1cc(-c2cnc3[nH]cc(-c4nnc(N(CC#N)c5ccccc5Cl)o4)c3c2)cn1]<br>((2-Chlorophenyl)-{5-[5-(1-methyl-1H-pyrazol-4-yl)-1H-pyrrolo-[2,3-b]pyridin-3-yl]-1,3,4-oxadiazol-2-yl}amino)acetonitrile |
| 50 | 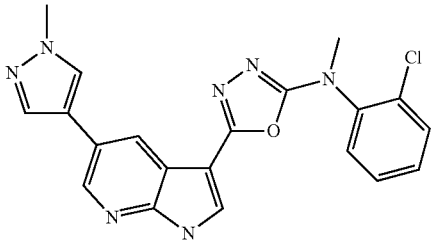<br>(2-Chlorophenyl)methyl-{5-[5-(1-methyl-1H-pyrazol-4-yl)-1H-pyrrolo[2,3-b]pyridin-3-yl]-1,3,4-oxadiazol-2-yl}amine |

| Compound No. | Name and/or structure |
|---|---|
| 51 | 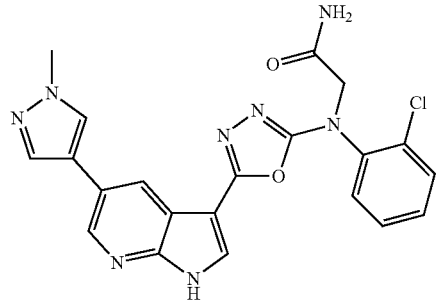 [SMILES: Cn1cc(-c2cnc3[nH]cc(-c4nnc(N(CC(N)=O)c5ccccc5Cl)o4)c3c2)cn1]<br>2-((2-Chlorophenyl)-{5-[5-(1-methyl-1H-pyrazol-4-yl)-1H-pyrrolo-[2,3-b]pyridin-3-yl]-1,3,4-oxadiazol-2-yl}amino)acetamide |
| 52 | 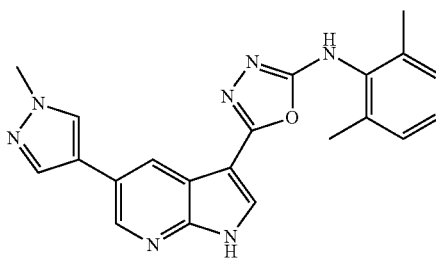<br>(2,6-Dimethylphenyl)-{5-[5-(1-methyl-1H-pyrazol-4-yl)-1H-pyrrolo-[2,3-b]pyridin-3-yl]-1,3,4-oxadiazol-2-yl}amine |
| 53 | 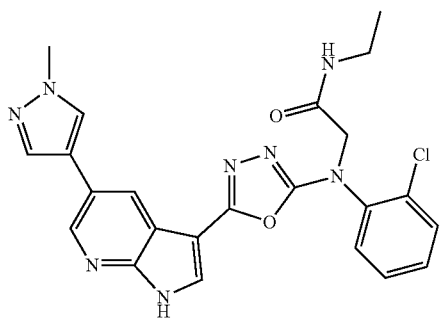 [SMILES: CCNC(=O)CN(c1nnc(-c2c[nH]c3ncc(-c4cnn(C)c4)cc23)o1)c1ccccc1Cl]<br>2-((2-Chlorophenyl)-{5-[5-(1-methyl-1H-pyrazol-4-yl)-1H-pyrrolo-[2,3-b]pyridin-3-yl]-1,3,4-oxadiazol-2-yl}amino)-N-ethylacetamide |
| 54 | 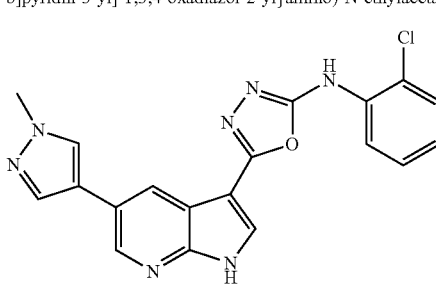<br>(2-Chlorophenyl)-{5- [5-(1-methyl-1H-pyrazol-4-yl)-1H-pyrrolo-[2,3-b]pyridin-3-yl]-1,3,4-oxadiazol-2-yl)amine |
| 55 | 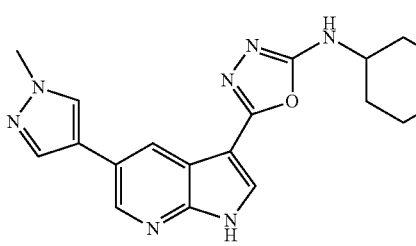<br>Cyclohexyl-{5-[5-(1-methyl-1H-pyrazol-4-yl)-1H-pyrrolo[2,3-b]-pyridin-3-yl]-1,3,4-oxadiazol-2-yl}amine |

| Compound No. | Name and/or structure |
|---|---|
| 56 | 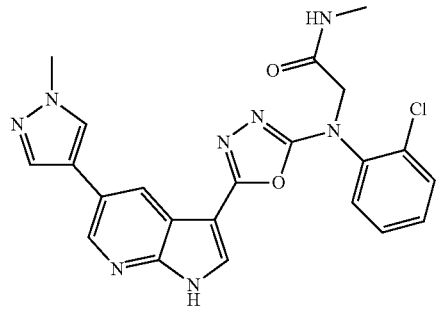 [SMILES: CNC(=O)CN(c1nnc(-c2c[nH]c3ncc(-c4cnn(C)c4)cc23)o1)c1ccccc1Cl]
2((2-Chlorophenyl)-{5-[5-(1-methyl-1H-pyrazol-4-yl)-1H-pyrrolo-[2,3-b]pyridin-3-yl]-1,3,4-oxadiazol-2-yl}amino)-N-methylacetamide |
| 57 | 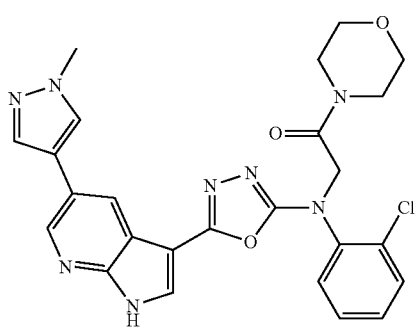 [SMILES: Cn1cc(-c2cnc3[nH]cc(-c4nnc(N(CC(=O)N5CCOCC5)c5ccccc5Cl)o4)c3c2)cn1]
2-((2-Chlorophenyl)-{5-[5-(1-methyl-1H-pyrazol-4-yl)-1H-pyrrolo-[2,3-b]pyridin-3-yl]-1,3,4-oxadiazol-2-yl}amino)-1-morpholin-4-ylethanone |
| 58 | 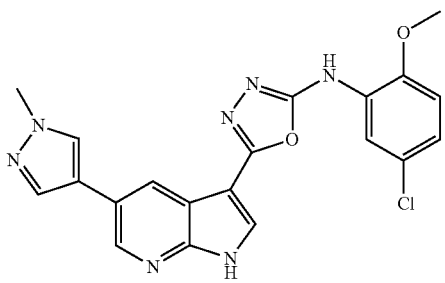 [SMILES: COc1ccc(Cl)cc1Nc1nnc(-c2c[nH]c3ncc(-c4cnn(C)c4)cc23)o1]
(5-Chloro-2-methoxyphenyl)-{5-[5-(1-methyl-1H-pyrazol-4-yl)-1H-pyrrolo[2,3-b]pyridin-3-yl]-1,3,4-oxadiazol-2-yl}amine |
| 59 | 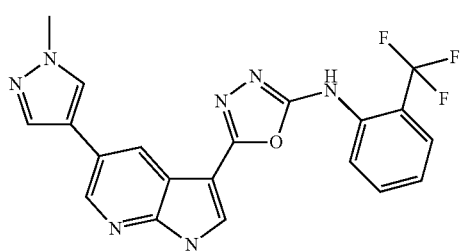
{5-[5-(1-Methyl-1H-pyrazol-4-yl)-1H-pyrrolo[2,3-b]pyridin-3-yl]-1,3,4-oxadiazol-2-yl}-(2-trifluoromethylphenyl)amine |

| Compound No. | Name and/or structure |
| --- | --- |
| 60 | 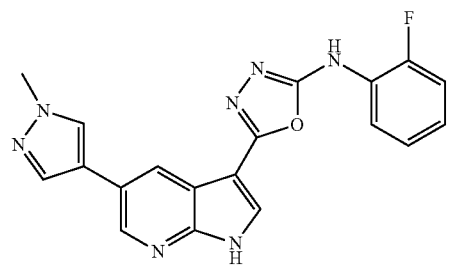 [SMILES: Cn1cc(-c2cnc3[nH]cc(-c4nnc(Nc5ccccc5F)o4)c3c2)cn1]<br>(2-Fluorophenyl)-{5-[5-(1-methyl-1H-pyrazol-4-yl)-1H-pyrrolo-[2,3-b]pyridin-3-yl]-1,3,4-oxadiazol-2-yl}amine |
| 61 | 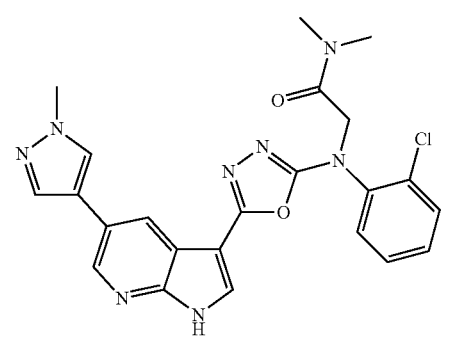 [SMILES: CN(C)C(=O)CN(c1nnc(-c2c[nH]c3ncc(-c4cnn(C)c4)cc23)o1)c1ccccc1Cl]<br>2((2-Chlorophenyl)-{5-[5-(1-methyl-1H-pyrazol-4-yl)-1H-pyrrolo-[2,3-b]pyridin-3-yl]-1,3,4-oxadiazol-2-yl}amino)-N,N-dimethylacetamide |
| 62 | 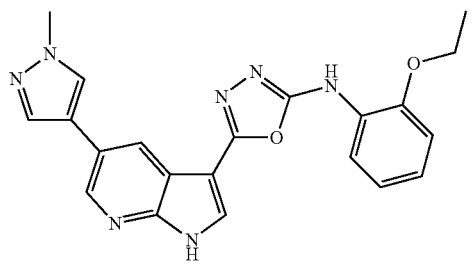 [SMILES: CCOc1ccccc1Nc1nnc(-c2c[nH]c3ncc(-c4cnn(C)c4)cc23)o1]<br>(2-Ethoxyphenyl)-{5-[5-(1-methyl-1H-pyrazol-4-yl)-1H-pyrrolo-[2,3-b]pyridin-3-yl]-1,3,4-oxadiazol-2-yl}amine |
| 63 | 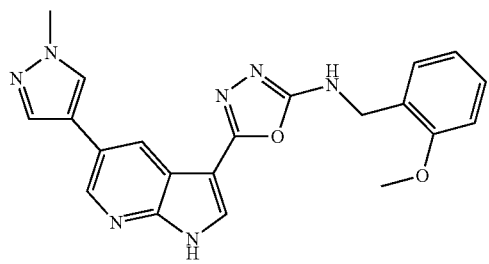 [SMILES: COc1ccccc1CNc1nnc(-c2c[nH]c3ncc(-c4cnn(C)c4)cc23)o1]<br>(2-Methoxybenzyl)-{5-[5-(1-methyl-1H-pyrazol-4-yl)-1H-pyrrolo-[2,3-b]pyridin-3-yl]-1,3,4-oxadiazol-2-yl}amine |

| Compound No. | Name and/or structure |
|---|---|
| 64 | 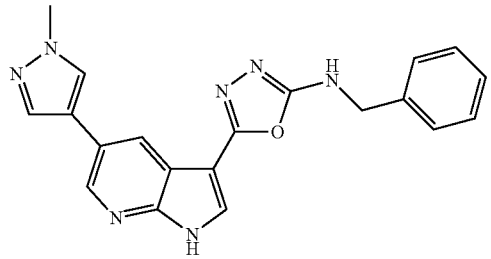 [SMILES: Cn1cc(-c2cnc3[nH]cc(-c4nnc(NCc5ccccc5)o4)c3c2)cn1]
Benzyl-{5-[5-(1-methyl-1H-pyrazol-4-yl)-1H-pyrrolo[2,3-b]pyridin-3-yl]-1,3,4-oxadiazol-2-yl}amine |
| 65 | 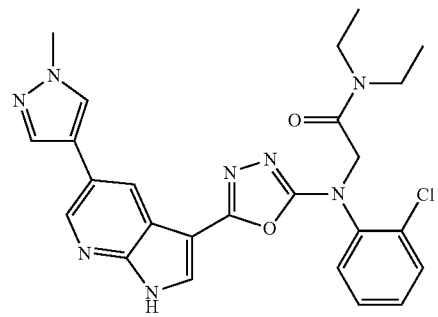 [SMILES: CCN(CC)C(=O)CN(c1nnc(-c2c[nH]c3ncc(-c4cnn(C)c4)cc23)o1)c1ccccc1Cl]
2-((2-Chlorophenyl)-{5-[5-(1-methyl-1H-pyrazol-4-yl)-1H-pyrrolo-[2,3-b]pyridin-3-yl]-1,3,4-oxadiazol-2-yl}amino)-N,N-diethylacetamide |
| 66 | 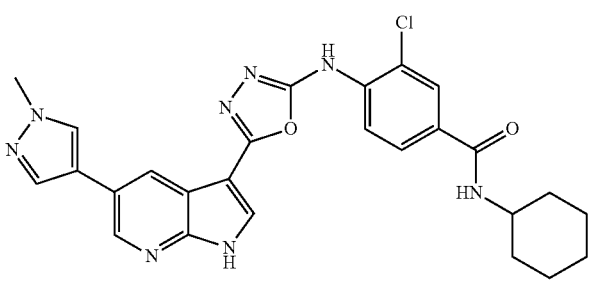 [SMILES: Cn1cc(-c2cnc3[nH]cc(-c4nnc(Nc5ccc(C(=O)NC6CCCCC6)cc5Cl)o4)c3c2)cn1]
3-Chloro-N-cyclohexyl-4-{5-[5-(1-methyl-1H-pyrazol-4-yl)-1H-pyrrolo[2,3-b]pyridin-3-yl]-1,3,4-oxadiazol-2-ylamino}benzamide |
| 67 | 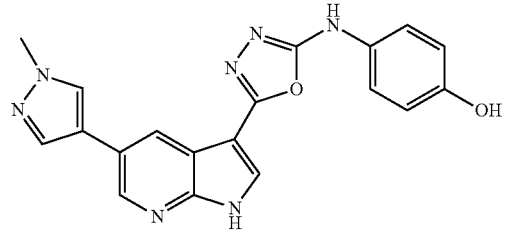 [SMILES: Cn1cc(-c2cnc3[nH]cc(-c4nnc(Nc5ccc(O)cc5)o4)c3c2)cn1]
4-{5-[5-(1-Methyl-1H-pyrazol-4-yl)-1H-pyrrolo[2,3-b]pyridin-3-yl]-1,3,4-oxadiazol-2-ylamino}phenol |

| Compound No. | Name and/or structure |
|---|---|
| 68 | 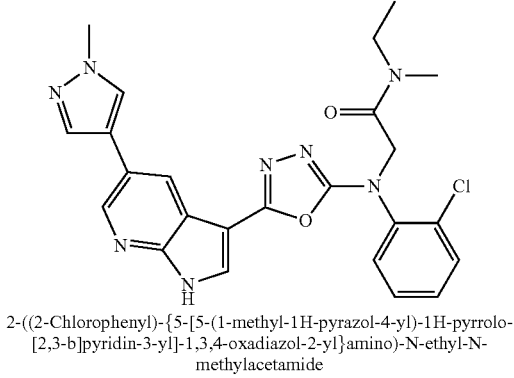
2-((2-Chlorophenyl)-{5-[5-(1-methyl-1H-pyrazol-4-yl)-1H-pyrrolo-[2,3-b]pyridin-3-yl]-1,3,4-oxadiazol-2-yl}amino)-N-ethyl-N-methylacetamide |
| 69 | 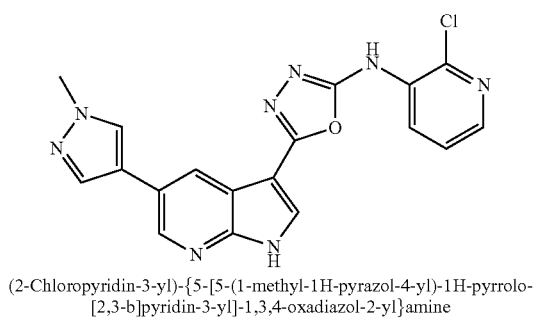
(2-Chloropyridin-3-yl)-{5-[5-(1-methyl-1H-pyrazol-4-yl)-1H-pyrrolo-[2,3-b]pyridin-3-yl]-1,3,4-oxadiazol-2-yl}amine |
| 70 | 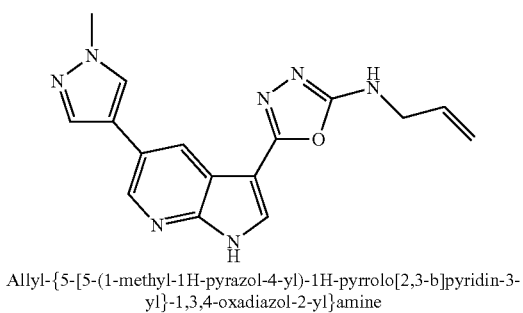
Allyl-{5-[5-(1-methyl-1H-pyrazol-4-yl)-1H-pyrrolo[2,3-b]pyridin-3-yl}-1,3,4-oxadiazol-2-yl}amine |
| 71 | 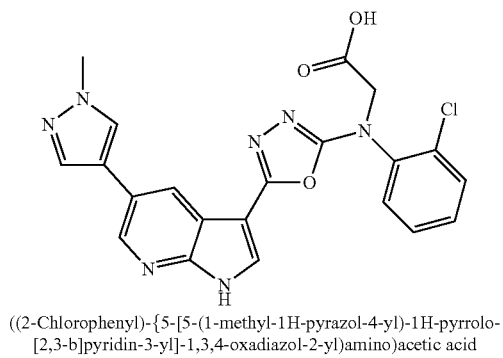
((2-Chlorophenyl)-{5-[5-(1-methyl-1H-pyrazol-4-yl)-1H-pyrrolo-[2,3-b]pyridin-3-yl]-1,3,4-oxadiazol-2-yl)amino)acetic acid |

| Compound No. | Name and/or structure |
|---|---|
| 72 | 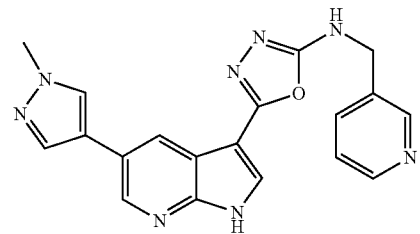 [SMILES: Cn1cc(-c2cnc3[nH]cc(-c4nnc(NCc5cccnc5)o4)c3c2)cn1]
{5[5-(1-Methyl-1H-pyrazol-4-yl)-1H-pyrrolo[2,3-b]pyridin-3-yl]-1,3,4-oxadiazol-2-yl}pyridin-3-ylmethylamine |
| 73 | 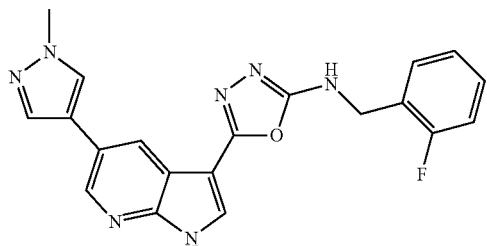
(2-Fluorobenzyl)-{5-[5-(1-methyl-1H-pyrazol-4-yl)-1H-pyrrolo-[2,3-b]pyridin-3-yl]-1,3,4-oxadiazol-2-yl}amine |
| 74 | 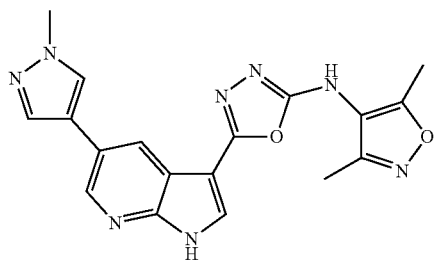 [SMILES: Cc1noc(C)c1Nc1nnc(-c2c[nH]c3ncc(-c4cnn(C)c4)cc23)o1]
(3,5-Dimethylisoxazol-4-yl)-{5-[5-(1-methyl-1H-pyrazol-4-yl)-1H-pyrrolo[2,3-b]pyridin-3-yl]-1,3,4-oxadiazol-2-yl}amine |
| 75 | 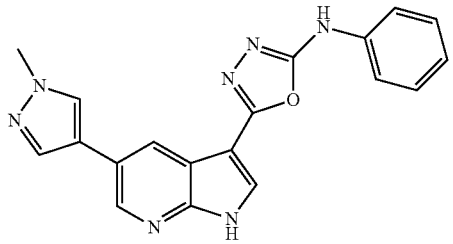 [SMILES: Cn1cc(-c2cnc3[nH]cc(-c4nnc(Nc5ccccc5)o4)c3c2)cn1]
{5-[5-(1-Methyl-1H-pyrazol-4-yl)-1H-pyrrolo[2,3-b]pyridin-3-y]-1,3,4-oxadiazol-2-yl}phenylamine |
| 76 | 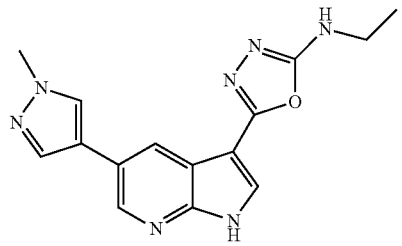 [SMILES: CCNc1nnc(-c2c[nH]c3ncc(-c4cnn(C)c4)cc23)o1]
Ethyl-{5-[5-(1-methyl-1H-pyrazol-4-yl)-1H-pyrrolo[2,3-b]pyridin-3-yl]-1,3,4-oxadiazol-2-yl}amine |

-continued

| Compound No. | Name and/or structure |
|---|---|
| 77 | 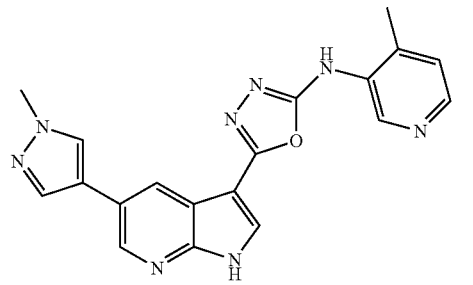 [SMILES: Cc1ccncc1Nc1nnc(-c2c[nH]c3ncc(-c4cnn(C)c4)cc23)o1]<br>{5-[5-(1-Methyl-1H-pyrazol-4-yl)-1H-pyrrolo[2,3-b]pyridin-3-yl]-1,3,4-oxadiazol-2-yl]-(4-methylpyridin-3-yl)amine |
| 78 | 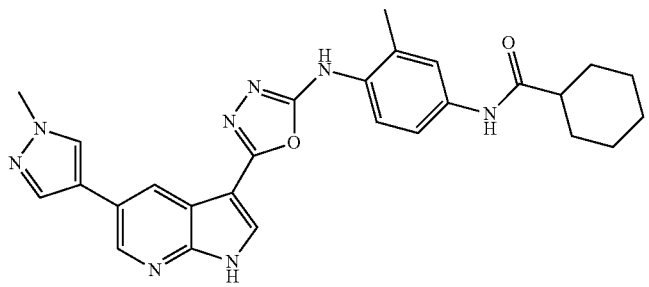 [SMILES: Cc1cc(NC(=O)C2CCCCC2)ccc1Nc1nnc(-c2c[nH]c3ncc(-c4cnn(C)c4)cc23)o1]<br>N-(3-Methyl-4-{5-[5-(1-methyl-1H-pyrazol-4-yl)-1H-pyrrolo[2,3-b]-pyridin-3-yl]-1,3,4-oxadiazol-2-ylamino}phenyl)cyclohexane-carboxamide |
| 79 | 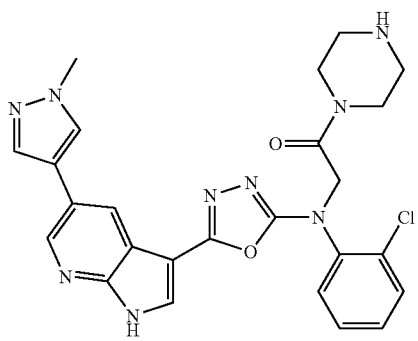 [SMILES: Cn1cc(-c2cnc3[nH]cc(-c4nnc(N(CC(=O)N5CCNCC5)c5ccccc5Cl)o4)c3c2)cn1]<br>2-((2-Chlorophenyl)-{5-[5-(1-methyl-1H-pyrazol-4-yl)-1H-pyrrolo-[2,3-b]pyridin-3-yl]-1,3,4-oxadiazol-2-yl}amino)-1-piperazin-1-ylethanone |
| 81 | 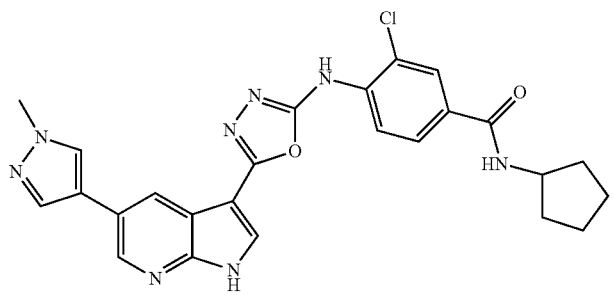 [SMILES: Cn1cc(-c2cnc3[nH]cc(-c4nnc(Nc5ccc(C(=O)NC6CCCC6)cc5Cl)o4)c3c2)cn1]<br>3-Chloro-N-cyclopentyl-4-{5-[5-(1-methyl-1H-pyrazol-4-yl)-1H-pyrrolo[2,3-b]pyridin-3-yl]-1,3,4-oxadiazol-2-ylamino}benzamide |

| Compound No. | Name and/or structure |
|---|---|
| 82 | 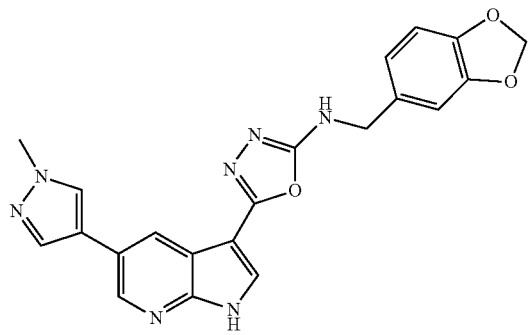 [SMILES: Cn1cc(-c2cnc3[nH]cc(-c4nnc(NCc5ccc6c(c5)OCO6)o4)c3c2)cn1]<br>Benzo-1,3-dioxol-5-ylmethyl-{5-[5-(1-methyl-1H-pyrazol-4-yl)-1H-pyrrolo[2,3-b]pridin-3-yl]-1,3,4-oxadiazol-2-yl}amine |
| 83 | 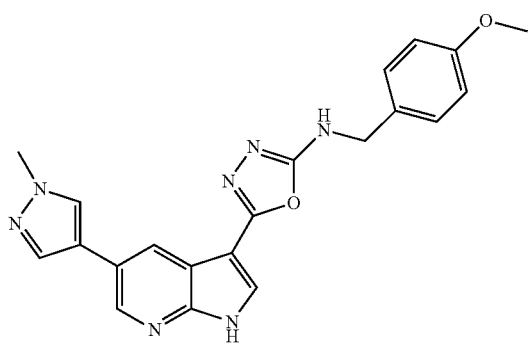 [SMILES: COc1ccc(CNc2nnc(-c3c[nH]c4ncc(-c5cnn(C)c5)cc34)o2)cc1]<br>(4-Methoxybenzyl)-{5-[5-(1-methyl-1H-pyrazol-4-yl)-1H-pyrrolo-[2,3-b]pyridin-3-yl]-1,3,4-oxadiazol-2-yl}amine |
| 84 | 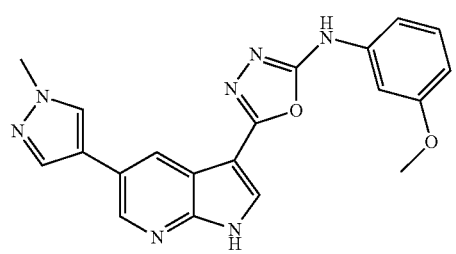 [SMILES: COc1cccc(Nc2nnc(-c3c[nH]c4ncc(-c5cnn(C)c5)cc34)o2)c1]<br>(3-Methoxyphenyl)-{5-[5-(1-methyl-1H-pyrazol-4-yl)-1H-pyrrolo-[2,3-b]pyridin-3-yl]-1,3,4-oxadiazol-2-yl)amine |
| 85 | 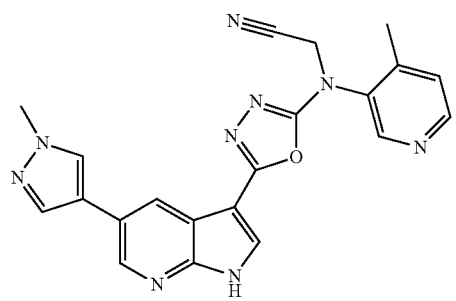 [SMILES: Cc1ccncc1N(CC#N)c1nnc(-c2c[nH]c3ncc(-c4cnn(C)c4)cc23)o1]<br>[{5-[5-(1-Methyl-1H-pyrazol-4-yl)-1H-pyrrolo[2,3-b]pyridin-3-yl]-1,3,4-oxadiazol-2-yl}-2-methylpyridin-3-yl)amino]acetonitrile |

| Compound No. | Name and/or structure |
|---|---|
| 86 | 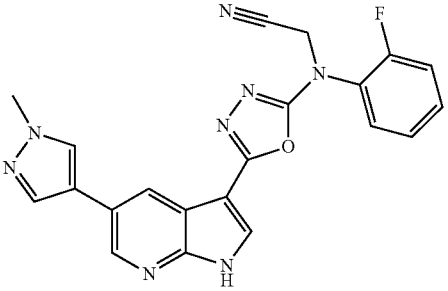 [SMILES: Cn1cc(-c2cnc3[nH]cc(-c4nnc(N(CC#N)c5ccccc5F)o4)c3c2)cn1]<br>((2-Fluorophenyl)-{5-[5-(1-methyl-1H-pyrazol-4-yl)-1H-pyrrolo-[2,3-b]pyridin-3-yl]-1,3,4-oxadiazol-2-yl}amino)acetonitrile |
| 87 | 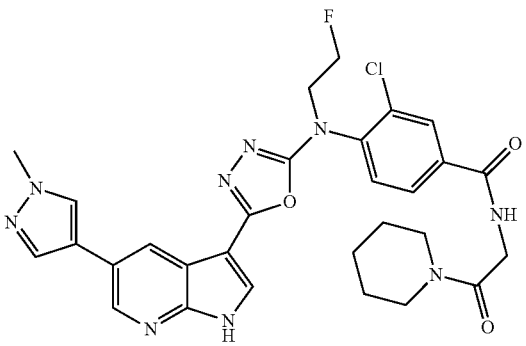 [SMILES: Cn1cc(-c2cnc3[nH]cc(-c4nnc(N(CCF)c5ccc(C(=O)NCC(=O)N6CCCCC6)cc5Cl)o4)c3c2)cn1]<br>3-Chloro-4-((2-fluoroethyl)-{5-[5-(1-methyl-1H-pyrazol-4-yl)-1H-pyrrolo[2,3-b]pyridin-3-yl]-1,3,4-oxadiazol-2-ylamino}-N-(2-oxo-2-piperidin-1-ylethyp)benzamide |
| 87a | 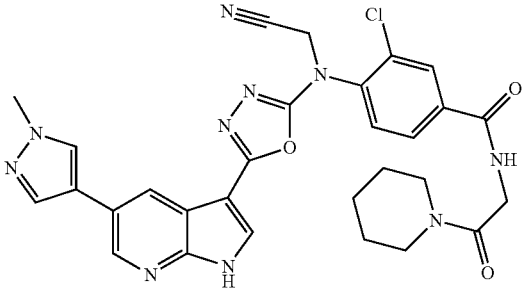 [SMILES: Cn1cc(-c2cnc3[nH]cc(-c4nnc(N(CC#N)c5ccc(C(=O)NCC(=O)N6CCCCC6)cc5Cl)o4)c3c2)cn1]<br>3-Chloro-4-(cyanomethyl-{5-[5-(1-methyl-1H-pyrazol-4-yl)-1H-pyrrolo[2,3-b]pyridin-3-yl]-1,3,4-oxadiazol-2-yl}amino)-N-(2-oxo-2-piperidin-1-ylethyl)benzamide | or pharmaceutically acceptable salts, tautomers and stereoisomers thereof.

6. A process for preparing the compound of the formula I according to claim 1 or a pharmaceutically acceptable salt, tautomer or stereoisomer thereof, comprising (a)

(1) reacting a compound of formula II

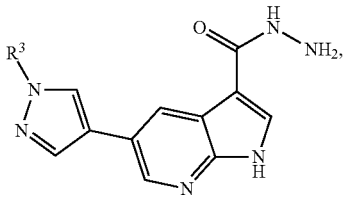

II

In which $R^3$ denotes the same structure as indicated in the compound of formula I, with a compound of formula III, $$R^2\text{—}N\text{=}C\text{=}S \qquad \text{III,}$$

in which $R^2$ denotes the same structure as indicated in the compound of formula I, to prepare a compound of formula I in which $R^1$ is H, or (2) converting the base or acid compound of the formula I of step (a) (1) into one of its salts or
(b)
(1) reacting a compound formula IV,

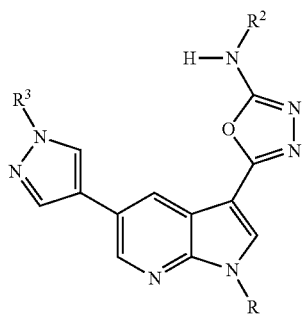

in which $R^2$ and $R^3$ denote the same respective structures as indicated in the compound of formula I and
R denotes an amino-protecting group,
with a compound of formula V $R^1$-L    V in which L denotes Cl, Br, I, tosylate or mesylate,
and (2) cleaving off the amino-protecting group at the same time or subsequently,
to prepare a compound of formula I in which $R^1$ denotes A, $CH_2CN$, $CH_2CONH_2$, $CH_2CONHA'$, $CH_2CONA'_2$, $CH_2COOH$, $CH_2COOA'$ or $CH_2COHet'$,
or
(3) converting the base or acid compound of the formula I of step (b) (2) into one of its salts.

7. A pharmaceutical composition comprising at least one compound of the formula I according to claim 1 and/or a pharmaceutically acceptable salt, tautomer or stereoisomer thereof, and one or more pharmaceutically acceptable excipients and/or adjuvants.

8. A compound, which is [3-chloro-1-(2-fluoroethyl)-1H-pyridin-(4E)-ylidene]-{5-[5-(1-methyl-1H-pyrazol-4-yl)-1H-pyrrolo[2,3-b]pyridin-3-yl]-1,3,4-oxadiazol-2-yl}amine

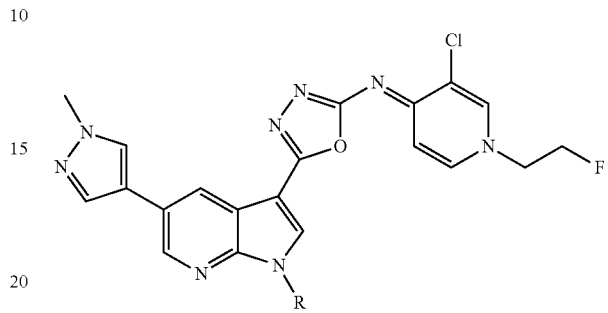

or a pharmaceutically acceptable salt, tautomer or stereoisomer thereof.

9. A pharmaceutical composition comprising at least one compound of claim 5 and/or a pharmaceutically acceptable salt, tautomer or stereoisomer thereof, and one or more pharmaceutically acceptable excipients and/or adjuvants.

10. A pharmaceutical composition comprising at least one compound of claim 8 and/or a pharmaceutically acceptable salt, tautomer or stereoisomer thereof, and one or more pharmaceutically acceptable excipients and/or adjuvants.

* * * * *

UNITED STATES PATENT AND TRADEMARK OFFICE
CERTIFICATE OF CORRECTION

PATENT NO. : 8,993,564 B2  Page 1 of 2
APPLICATION NO. : 14/126857
DATED : March 31, 2015
INVENTOR(S) : Timo Heinrich et al.

It is certified that error appears in the above-identified patent and that said Letters Patent is hereby corrected as shown below:

IN THE CLAIMS:

Column 70, lines 52-65 (Claim 1), the compound of formula I presents as:

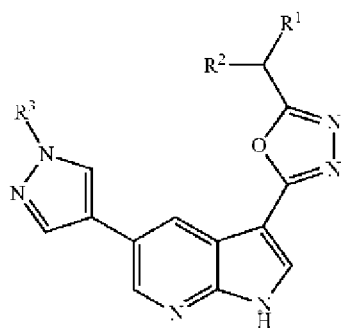

Should present as:

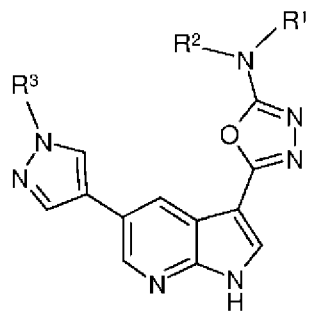

Column 72, line 24 (Claim 4), reads as: -- $(CH_2)_2COOA$, $(CH_2)_2OH$, $(CH_2)_2OA$, $COHet^1$, --
Should read: -- $(CH_2)_2COOA$, $(CH_2)_2OH$, $(CH_2)_2OA$, $COHet^1$, --.

Signed and Sealed this
Twentieth Day of October, 2015

Michelle K. Lee
*Director of the United States Patent and Trademark Office*

CERTIFICATE OF CORRECTION (continued)
U.S. Pat. No. 8,993,564 B2

Column 101, (Claim 5), Compound 85 presents as:

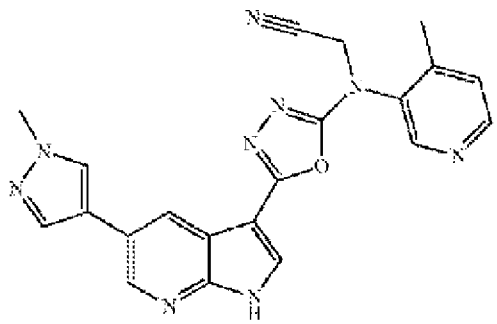

Should present as:

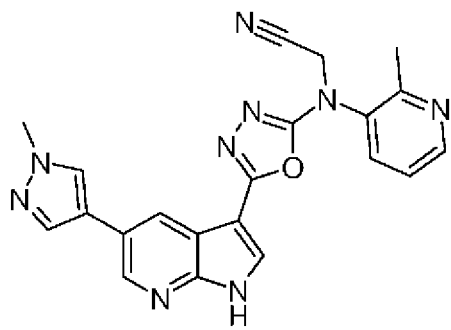

Column 106, lines 10-22 (Claim 8), The compound presents as:

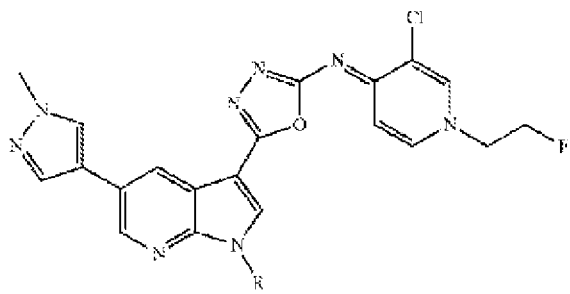

Should present as: